(12) United States Patent
Miller-Kovach et al.

(10) Patent No.: US 8,382,482 B2
(45) Date of Patent: Feb. 26, 2013

(54) PROCESSES AND SYSTEMS FOR ACHIEVING AND ASSISTING IN IMPROVED NUTRITION BASED ON FOOD ENERGY DATA AND RELATIVE HEALTHFULNESS DATA

(75) Inventors: Karen Miller-Kovach, Charleston, SC (US); Ute Gerwig, Düsseldorf (DE); Julia Peetz, Düsseldorf (DE); Christine Jacobsohn, Düsseldorf (DE); Wanema Frye, Overland Park, KS (US); Stephanie Lyn Rost, Jersey City, NJ (US); Maria Kinirons, East Islip, NY (US); Dawn Halkuff, New York, NY (US)

(73) Assignee: Weight Watchers International, Inc., New York, NY (US)

( * ) Notice: Subject to any disclaimer, the term of this patent is extended or adjusted under 35 U.S.C. 154(b) by 744 days.

(21) Appl. No.: 12/550,240

(22) Filed: Aug. 28, 2009

(65) Prior Publication Data

US 2010/0080875 A1    Apr. 1, 2010

Related U.S. Application Data

(60) Provisional application No. 61/092,981, filed on Aug. 29, 2008.

(51) Int. Cl.
*G09B 19/00*    (2006.01)
(52) U.S. Cl. ............ 434/127; 128/921; 426/87; 426/106
(58) Field of Classification Search .................. 434/127; 128/921; 707/732, 784; 426/87, 106
See application file for complete search history.

(56) References Cited

U.S. PATENT DOCUMENTS

| | | | |
|---|---|---|---|
| 3,769,720 | A | 11/1973 | Terrones |
| 4,686,624 | A | 8/1987 | Blum et al. |
| 4,891,756 | A | 1/1990 | Williams, III |
| 5,412,560 | A | 5/1995 | Dennision |
| 5,412,564 | A | 5/1995 | Ecer |
| 5,478,989 | A | 12/1995 | Shepley |
| 5,558,742 | A | 9/1996 | Kiefer |
| 5,704,350 | A | 1/1998 | Williams |
| 5,819,735 | A | 10/1998 | Mansfield et al. |
| 6,040,531 | A | 3/2000 | Miller-Kovach et al. |
| 6,283,914 | B1 | 9/2001 | Mansfield et al. |

(Continued)

FOREIGN PATENT DOCUMENTS

| | | |
|---|---|---|
| AU | 717127 | 12/1997 |
| AU | 714860 | 1/2000 |

(Continued)

OTHER PUBLICATIONS

International Search Report in PCT/US09/55411 dated Oct. 20, 2009.

(Continued)

*Primary Examiner* — Xuan Thai
*Assistant Examiner* — Bruk Gebremichael
(74) *Attorney, Agent, or Firm* — Greenberg Traurig, LLP

(57) ABSTRACT

Processes are provided for controlling body weight of a consumer, as well as for selecting and purchasing foods, and for producing food products, based on a combination of food energy data and relative healthfulness data for a candidate food. Various ways are provided for obtaining and accessing the food energy data and relative healthfulness data. Related processes and systems are also provided for assisting in the foregoing processes.

21 Claims, 21 Drawing Sheets

U.S. PATENT DOCUMENTS

| | | | |
|---|---|---|---|
| 6,553,386 B1 | 4/2003 | Alabaster | |
| 6,663,564 B2 | 12/2003 | Miller-Kovach et al. | |
| 6,811,516 B1 | 11/2004 | Dugan | |
| 6,872,077 B2* | 3/2005 | Yeager | 434/127 |
| 6,878,885 B2 | 4/2005 | Miller-Kovatch et al. | |
| 6,953,342 B2 | 10/2005 | Bisogno | |
| 6,978,221 B1 | 12/2005 | Rudy | |
| 6,980,999 B1 | 12/2005 | Grana | |
| 7,189,191 B2 | 3/2007 | Dugan | |
| 7,247,023 B2 | 7/2007 | Peplinski et al. | |
| 7,297,109 B2 | 11/2007 | Brown | |
| 7,361,143 B2 | 4/2008 | Kirchhoff et al. | |
| 7,432,454 B1* | 10/2008 | Sze et al. | 177/25.16 |
| 7,680,690 B1* | 3/2010 | Catalano | 705/15 |
| 7,959,567 B2 | 6/2011 | Stivoric | |
| 7,974,881 B2 | 7/2011 | Culver et al. | |
| 2002/0046060 A1 | 4/2002 | Hoskyns et al. | |
| 2003/0171944 A1 | 9/2003 | Fine et al. | |
| 2003/0187683 A1 | 10/2003 | Kirchhoff et al. | |
| 2003/0208409 A1 | 11/2003 | Mault | |
| 2004/0171925 A1 | 9/2004 | Kirchhoff et al. | |
| 2004/0210456 A1 | 10/2004 | Kirchhoff et al. | |
| 2005/0021361 A1 | 1/2005 | Huang et al. | |
| 2005/0031671 A1 | 2/2005 | Johnson | |
| 2005/0113649 A1 | 5/2005 | Bergantino | |
| 2005/0240434 A1 | 10/2005 | Wooten et al. | |
| 2006/0058586 A1 | 3/2006 | Humble | |
| 2006/0064447 A1* | 3/2006 | Malkov | 708/200 |
| 2006/0122468 A1* | 6/2006 | Tavor | 600/300 |
| 2006/0178907 A1 | 8/2006 | Humble | |
| 2006/0263750 A1 | 11/2006 | Gordon | |
| 2007/0038933 A1 | 2/2007 | Luzzatto | |
| 2007/0135266 A1 | 6/2007 | Dugan | |
| 2007/0143126 A1 | 6/2007 | Ghose | |
| 2007/0218107 A1 | 9/2007 | Schur et al. | |
| 2008/0059342 A1 | 3/2008 | Culver et al. | |
| 2008/0124447 A1 | 5/2008 | Shortall | |
| 2008/0177572 A1 | 7/2008 | Fuhrman et al. | |
| 2009/0298021 A1 | 12/2009 | Black et al. | |
| 2010/0055271 A1 | 3/2010 | Miller-Kovach et al. | |
| 2010/0055652 A1 | 3/2010 | Miller-Kovach et al. | |
| 2010/0055653 A1 | 3/2010 | Miller-Kovach et al. | |
| 2010/0062119 A1 | 3/2010 | Miller-Kovach et al. | |
| 2010/0062402 A1 | 3/2010 | Miller-Kovach et al. | |

FOREIGN PATENT DOCUMENTS

| | | |
|---|---|---|
| AU | 752986 | 10/2002 |
| AU | 2003230179 | 12/2003 |
| AU | 2005249060 | 12/2005 |
| AU | 2005203248 | 2/2006 |
| AU | 2006100046 | 4/2006 |
| AU | 2007221968 | 11/2007 |
| DE | 197 25 676 | 12/1998 |
| DE | 10 2004 040 308 | 3/2006 |
| DE | 202005018461 | 5/2006 |
| EP | 0 128 054 | 12/1984 |
| EP | 0 409 231 | 5/1997 |
| EP | 0 990 991 | 5/2000 |
| EP | 1 030 245 | 8/2000 |
| EP | 1 462 979 | 9/2004 |
| EP | 1 758 038 | 2/2007 |
| FR | 2 718 265 | 3/1994 |
| GB | 2 288 257 | 10/1995 |
| GB | 2 399 428 | 9/2004 |
| GB | 2 414 844 | 12/2005 |
| GB | 2 419 704 | 5/2006 |
| GB | 2 420 428 | 5/2006 |
| GB | 2 439 670 | 1/2008 |
| WO | 93/07570 | 4/1993 |
| WO | 98/45766 | 10/1998 |
| WO | 98/45766 A1 | 10/1998 |
| WO | 00/58851 | 10/2000 |
| WO | 01/89365 | 11/2001 |
| WO | 02/065336 | 8/2002 |
| WO | 03/067373 | 8/2003 |
| WO | 03/103485 | 12/2003 |
| WO | 2004/019264 | 3/2004 |
| WO | 2006/054100 | 5/2006 |
| WO | 2006/081073 | 8/2006 |
| WO | 2007/077253 | 7/2007 |
| WO | 2007/77253 | 7/2007 |
| WO | 2007/137110 | 11/2007 |
| WO | 2008/020831 | 2/2008 |

OTHER PUBLICATIONS

International Search Report in PCT/US09/55311 dated Oct. 14, 2009.

International Search Report in PCT/US09/55350 dated Oct. 20, 2009.

International Search Report in PCT/US09/55445 dated Mar. 4, 2010.

International Search Report in PCT/US09/55242 dated Mar. 3, 2010.

International Search Report in PCT/US09/55244 dated Oct. 22, 2009.

Singletary et al., "Alcohol and Breast Cancer: Review of Epidemiologic and Experimental Evidence and Potential Mechanisms", JAMA, Nov. 7, 2001—vol. 286, No. 17, pp. 2143-2151.

Flatt, "Body composition, respiratory quotient, and weight maintenance", AM J Clin Nutr 1995:62 (suppl): pp. 1107S-1117S.

2005 Dietary Guidelines Advisory Committee Report, Part D: Science Base, Section 5: Carbohydrates, pp. 1-30.

Rolls, "Carbohydrates, fats, and satiety", Am J Nutr 1995:61(suppl): pp. 960S-9607S.

Schutz et al., Decreased glucose-induced thermogenesis after weight loss in obese subjects: a predisposing factor for relapse of obesity?, The American Journal of Clinical Nutrition 36: Mar. 1984, pp. 380-387.

Hu et al., "Diet and risk of Type II diabetes: the role of types of fat and carbohydrate", Diabetologia (2001) 44: pp. 805-817.

Karst et al., "Diet-Induced Thermogenesis in Man: Thermic Effects of Single Proteins, Carbohydrates and Fats Depending on Their Energy Amount", Ann. Nutr. Metab. 28: 245-252 (1984).

Timm et al., "Dietary Fiber and the Relationship to Chronic Diseases", American Journal of Lifestyle Medicine, vol. 2, No. 3, 2008, pp. 233-240.

Hu et al., "Types of Dietary Fat and Risk of Coronary Heart Disease: A Critical Review", Journal of the American College of Nutrition, vol. 20, No. 1, 5-19 (2001).

Nelson et al., "Effect of weight reduction on resting energy expenditure, substrate utilization, and the thermic effect of food in moderately obese women", Am J Clin Nutr 1992: 55: 924-33.

2005 Dietary Guidelines Advisory Committee Report, Part D: Science Base, Section 8: Ethanol, pp. 1-14.

Schutz et al., "Exercise and postprandial thermogenesis in obese women before and after weight loss", Am J Clin Nutr 1987; 45: 1424-32.

2005 Dietary Guidelines Advisory Committee Report, Part D: Science Base, Section 4: Fats, pp. 1-54.

2005 Dietary Guidelines Advisory Committee Report, Part D: Science Base, Section 8: Fluid and Electrolytes, pp. 1-18.

Parker et al., "Effect of a High-Protein, High-Monounsaturated Fat Weight Loss Diet on Glycemic Control and Lipid Levels in Type 2 Diabetes", Diabetes Care, vol. 25, No. 3, Mar. 2002, pp. 425-430.

Simpson et al., "Macronutrients have different metabolic effects in nondiabetics and diabetics", The American Journal of Clinical Nutrition 42: Sep. 1985, pp. 449-453.

Reed et al., "Measuring the thermic effect of food", Am J Clin Nutr 1996; 63: 164-9.

Pi-Sunyer, "Metabolic Efficiency of Macronutrient Utilization in Humans", Critical Reviews in Food Science and Nutrition, 33(4/5): 359-361 (1993).

Melanson, "Nutrition for Women in the Prevention and Treatment of Type 2 Diabetes and Cardiovascular Diseases", American Journal of Lifestyle Medicine, May/Jun. 2008, vol. 2, No. 3, pp. 214-218.

Herder et al., "The Power of a Balanced Diet and Lifestyle in Preventing Cardiovascular Disease", Nutr Clin Care, Apr.-Jun. 2004, vol. 7, No. 2, pp. 46-55.

Acheson et al., "Nutritional influences on lipogenesis and thermogenesis after a carbohydrate meal", The American Physiological Society, 1984, pp. E62-E70.

Jequier, "Pathways to obesity", International Journal of Obesity (2002) 26, Suppl 2, pp. S12-S15.
Fodor et al., "Recommendations on dietary salt", CMAJ, May 4, 1999; 160 (9 Suppl), pp. S29-S34.
Den Besten et al., "Resting metabolic rate and diet-induced thermogenesis in abdominal and gluteal-femoral obese women before and after weight reduction", The American Journal of Clinical Nutrition 1998; 47, pp. 840-847.
Bennett et al., "Short-term effects of dietary-fat ingestion on energy expenditure and nutrient balance", The American Journal of Clinical Nutrition 1992; 55, pp. 1071-1077.
Murlin et al., "The Specific Dynamic Action of Butter Fat, and of Superimposed Sugar", The Journal of Nutrition, vol. 12, No. 6, Jul. 15, 1936, pp. 613-644.
Granata et al., "The Thermic Effect of Food and Obesity: Discrepant Results and Methodological Variations", Nutritional Reviews, vol. 60, No. 8, Aug. 2002, pp. 223-233.
Tappy, "Thermic effect of food and sympathetic nervous system activity in humans", Reprod Nutr Dev (1996) 36, pp. 391-397.
Glickman et al., "The Total Specific Dynamic Action of High-Protein and High-Carbohydrate Diets on Human Subjects", Jan. 19, 1948, pp. 41-57.
Official Action issued in connection with U.S. Appl. No. 12/549,533 on May 10, 2012.
Official Action issued in connection with U.S. Appl. No. 12/549,721 on Jun. 11, 2012.
Official Action issued in connection with U.S. Appl. No. 12/549,958 on May 11, 2012.
Official Action issued in connection with U.S. Appl. No. 12/549,251 on Sep. 6, 2012.
Official Action issued in connection with U.S. Appl. No. 12/549,251 on Feb. 2, 2012.
Official Action issued in connection with U.S. Appl. No. 12/549,225 on Aug. 31, 2012.

* cited by examiner

FIGURE 1

| | Beans, dry & Legumes | Oils |
|---|---|---|
| Most Healthful | HD ≤ 1.42 | (None) |
| Less Healthful | 1.42 < HD ≤ 1.9 | (None) |
| Even Less Healthful | (None) | HD ≤ 3.4 |
| Least Healthful | (None) | HD > 3.4 |

FIGURE 1A

| | Beef (cooked) | Cookies | Cream & Creamers | Eggs | Frankfurters | Game (raw) | Game (cooked) | Lamb (cooked) |
|---|---|---|---|---|---|---|---|---|
| Most Healthful | HD ≤ 2.7 | (None) | HD ≤ 1.2 | HD ≤ 3.2 | (None) | HD ≤ 2.1 | HD ≤ 2.7 | HD ≤ 2.7 |
| Less Healthful | 2.7 < HD ≤ 3.66 | (None) | 1.2 < HD ≤ 1.5 | (None) | HD ≤ 1.8 | (None) | 2.7 < HD ≤ 3.66 | 2.7 < HD ≤ 3.66 |
| Even Less Healthful | 3.66 < HD ≤ 4.99 | HD ≤ 4.05 | 1.5 < HD ≤ 2.8 | (None) | 1.8 < HD ≤ 4.0 | (None) | 3.66 < HD ≤ 4.99 | 3.66 < HD ≤ 4.99 |
| Least Healthful | HD > 4.99 | HD > 4.05 | HD > 2.8 | (None) | HD > 4.0 | HD > 2.9 | HD > 4.99 | HD > 4.99 |

FIGURE 1B

| | Luncheon Meats | Pizza | Pork (raw) | Pork (cooked) | Sausage | Snacks - Pretzels | Veal (raw) | Veal (cooked) |
|---|---|---|---|---|---|---|---|---|
| Most Healthful | HD ≤ 1.74 | (None) | HD ≤ 1.72 | HD ≤ 2.68 | (None) | (None) | HD ≤ 1.3 | HD ≤ 2.51 |
| Less Healthful | 1.74 < HD ≤ 2.4 | (None) | 1.72 < HD ≤ 2.81 | 2.68 < HD ≤ 3.54 | (None) | HD ≤ 4.691 | 1.3 < HD ≤ 2.7 | 2.51 < HD ≤ 2.6 |
| Even Less Healthful | 2.4 < HD ≤ 3.8 | HD ≤ 4.287 | 2.81 < HD ≤ 4.3 | 3.54 < HD ≤ 4.99 | HD ≤ 3.9 | 4.691 < HD ≤ 5.6 | (None) | 2.6 < HD ≤ 4.7 |
| Least Healthful | HD > 3.8 | HD > 4.287 | HD > 4.3 | HD > 4.99 | HD > 3.9 | HD > 5.6 | (None) | HD > 4.7 |

FIGURE 2

| | Beverages | Alcoholic Beverages | Sweet Spreads – Jams, Syrups, Toppings & Nut Butters |
|---|---|---|---|
| Most Healthful | HD ≤ 0.017 | (None) | (None) |
| Less Healthful | 0.017 < HD ≤ 0.056 | (None) | (None) |
| Even Less Healthful | 0.056 < HD ≤ 0.191 | (All) | HD ≤ 0.59 |
| Least Healthful | HD > 0.191 | (None) | HD > 0.59 |

FIGURE 2A

| | Cheese, Dairy & non-Dairy, Hard | Cheese, Cottage & Cream |
|---|---|---|
| Most healthful | HD ≤ 2.11 | HD ≤ 1.05 |
| Less Healthful | 2.11 < HD ≤ 4.02 | 1.05 < HD ≤ 2.0 |
| Even Less Healthful | HD > 4.02 | HD > 2.0 |
| Least Healthful | (None) | (None) |

FIGURE 3

| | Breads | Bagels | Tortillas, Wraps | Breakfast – Pancakes, Waffles, Pastries | Vegetable Dishes |
|---|---|---|---|---|---|
| Most Healthful | HD ≤ 1.36 | HD ≤ 1.03 | HD ≤ 0.69 | (None) | (None) |
| Less Healthful | 1.36 < HD ≤ 2.59 | 1.03 < HD ≤ 2.59 | 0.69 < HD ≤ 2.56 | (None) | HD ≤ 1.3087 |
| Even Less Healthful | 2.59 < HD ≤ 4.47 | 2.59 < HD ≤ 4.3 | 2.56 < HD ≤ 4.2 | HD ≤ 2.98 | 1.3087 < HD ≤ 2.152 |
| Least Healthful | HD > 4.47 | HD > 4.3 | HD > 4.2 | HD > 2.98 | HD > 2.152 |

FIGURE 3A

|  | Grains & Pasta, Cooked | Grains & Pastas, Uncooked |
|---|---|---|
| Most Healthful | HD ≤ 0.274 | HD ≤ 0.71 |
| Less Healthful | 0.274 < HD ≤ 0.43 | 0.71 < HD ≤ 1.22 |
| Even Less Healthful | 0.43 < HD ≤ 1.0 | 1.22 < HD ≤ 1.5 |
| Least Healthful | HD > 1.0 | HD > 1.5 |

FIGURE 4

| | Breakfast Cereals, hot, cooked | Breakfast Cereals, hot, uncooked | Fruit Salads, dishes |
|---|---|---|---|
| Most Healthful | HD ≤ 0.81 | HD ≤ 4.83 | (None) |
| Less Healthful | 0.81 < HD ≤ 0.92 | 4.83 < HD ≤ 6.1 | HD ≤ 2.0 |
| Even Less Healthful | HD > 0.92 | HD > 6.1 | HD > 2.0 |
| Least Healthful | (None) | (None) | (None) |

FIGURE 5

| | Bars | Cakes & Pastries | Candy |
|---|---|---|---|
| Most Healthful | (None) | (None) | (None) |
| Less Healthful | (None) | (None) | (None) |
| Even Less Healthful | HD ≤ 8.0 | HD ≤ 5.5 | HD ≤ 8.0 |
| Least Healthful | HD > 8.0 | HD > 5.5 | HD > 8.0 |

FIGURE 6

| | Dips | Dressings | Gravies | Sauces | Soups, Condensed | Soups, RTE | Spreads (other than sweet) |
|---|---|---|---|---|---|---|---|
| Most Healthful | HD ≤ 1.25 | HD ≤ 1.35 | (None) | HD ≤ 0.74 | HD ≤ 0.66 | HD ≤ 0.35 | HD ≤ 1.17 |
| Less Healthful | 1.25 < HD ≤ 1.66 | 1.35 < HD ≤ 3.6 | HD ≤ 0.6 | 0.74 < HD ≤ 1.53 | 0.66 < HD ≤ 1.22 | 0.35 < HD ≤ 0.944 | 1.17 < HD ≤ 3.6 |
| Even Less Healthful | 1.66 < HD ≤ 3.14 | 3.6 < HD ≤ 5.14 | 0.6 < HD ≤ 1.1 | 1.53 < HD ≤ 4.96 | 1.22 < HD ≤ 1.94 | 0.944 < HD ≤ 1.66 | 3.6 < HD ≤ 9.2 |
| Least Healthful | HD > 3.14 | HD > 5.14 | HD > 1.1 | HD > 4.96 | HD > 1.94 | HD > 1.66 | HD > 9.2 |

FIGURE 7

| | Beans, dry & Legumes Dishes | Beef Dishes | Breakfast Mixed Dishes | Cheese Dishes | Chili, Stew | Egg Dishes | Fish & Shellfish Dishes | Lamb Dishes | Pasta Dishes |
|---|---|---|---|---|---|---|---|---|---|
| Most Healthful | (None) | (None) | (None) | (None) | (None) | (None) | (None) | (None) | (None) |
| Less Healthful | $HD \leq 1.8$ | $HD \leq 1.8$ | $HD \leq 1.2$ | $HD \leq 1.8$ | $HD \leq 1.39$ | $HD \leq 1.8$ | $HD \leq 1.75$ | $HD \leq 1.8$ | $HD \leq 1.795$ |
| Even Less Healthful | $1.8 < HD \leq 3.0$ | $1.8 < HD \leq 3.002$ | $1.2 < HD \leq 4.46$ | $1.8 < HD \leq 3.0$ | $1.39 < HD \leq 1.93$ | $1.8 < HD \leq 3.0$ | $1.75 < HD \leq 3.0$ | $1.8 < HD \leq 3.002$ | $1.795 < HD \leq 3.0$ |
| Least Healthful | $HD > 3.0$ | $HD > 3.002$ | $HD > 4.46$ | $HD > 3.0$ | $HD > 1.93$ | $HD > 3.0$ | $3.0 < HD$ | $HD > 3.002$ | $HD > 3.0$ |

FIGURE 7A

| | Pasta, Cooked | Pork Dishes | Poultry Dishes | Rice & Grains Dishes | Salads, Main Course | Salads, Side | Sandwiches | Veal Dishes | Vegetarian Meat Substitutes |
|---|---|---|---|---|---|---|---|---|---|
| Most Healthful | $HD \leq -1.1$ | (None) | (None) | (None) | $HD \leq 0.64$ | $HD \leq 0.32$ | (None) | (None) | $HD \leq 1.47$ |
| Less Healthful | $-1.1 < HD \leq 0.12$ | $HD \leq 1.8$ | $HD \leq 1.77$ | $HD \leq 1.74$ | $0.64 < HD \leq 1.78$ | $0.32 < HD \leq 1.746$ | $HD \leq 1.8$ | $HD \leq 1.8$ | $1.47 < HD \leq 2.31$ |
| Even Less Healthful | $0.12 < HD \leq 0.52$ | $1.8 < HD \leq 3.0$ | $1.77 < HD \leq 3.0$ | $1.74 < HD \leq 3.0$ | $1.78 < HD \leq 3.0$ | $1.746 < HD \leq 3.0$ | $1.8 < HD \leq 3.0$ | $1.8 < HD \leq 3.0$ | $2.31 < HD \leq 4.84$ |
| Least Healthful | $HD > 0.52$ | $HD > 3.0$ | $HD > 3.0$ | $HD > 3.0$ | $HD > 3.0$ | $HD > 3.0$ | $HD > 3.0$ | $HD > 3.0$ | $HD > 4.84$ |

FIGURE 8

|  | Fruit – Fresh, Frozen & Dried | Fruit & Vegetable Juices |
|---|---|---|
| Most Healthful | HD ≤ 1.63 | (None) |
| Less Healthful | 1.63 < HD ≤ 6.2 | HD ≤ 1.2 |
| Even Less Healthful | 6.2 < HD ≤ 8.3 | HD > 1.2 |
| Least Healthful | HD > 8.3 | (None) |

FIGURE 8A

|  | Vegetables, Raw | Vegetables, Cooked |
|---|---|---|
| Most Healthful | HD < 4.1 | HD ≤ 1.57 |
| Less Healthful | HD > 4.1 | HD > 1.57 |
| Even Less Healthful | (None) | (None) |
| Least Healthful | (None) | (None) |

FIGURE 9

| | Gelatin, Puddings | Ice Cream Desserts | Ice Cream Novelties | Ice Cream, Sherbet, Sorbet | Sweet Pies | Sweets – Honey, Sugar, Syrup, Toppings |
|---|---|---|---|---|---|---|
| Most Healthful | HD ≤ 0.1 | (None) | (None) | (None) | (None) | HD ≤ 0.07 |
| Less Healthful | 0.1 < HD ≤ 1.6 | (None) | (None) | (None) | (None) | 0.07 < HD ≤ 1.2 |
| Even Less Healthful | 1.6 < HD ≤ 3.0 | HD ≤ 3.13 | HD ≤ 2.4 | HD ≤ 3.572 | HD ≤ 3.5 | 1.2 < HD ≤ 6.2 |
| Least Healthful | HD > 3.0 | HD > 3.13 | HD > 2.4 | HD > 3.572 | HD > 3.5 | HD > 6.2 |

PROCESSES AND SYSTEMS FOR ACHIEVING AND ASSISTING IN IMPROVED NUTRITION BASED ON FOOD ENERGY DATA AND RELATIVE HEALTHFULNESS DATA

BENEFIT AND RELATED APPLICATIONS

This application claims the benefit of U.S. provisional patent application No. 61/092,981, filed Aug. 29, 2008, in the names of Karen Miller-Kovach, Ute Gerwig, Julia Peetz, Christine Jacobsohn, Wanema Frye, Stephanie Lyn Rost and Maria Kinirons. The present application is related to U.S. patent application Ser. No. 12/549,225, filed Aug. 27, 2009, entitled Processes and Systems Based on Metabolic Conversion Efficiency; U.S. patent application Ser. No. 12/549,251, filed Aug. 27, 2009, entitled Processes and Systems Based on Dietary Fiber as Energy; U.S. patent application Ser. No. 12/549,533, filed Aug. 28, 2009, entitled Processes and Systems Using and Producing Food Healthfulness Data based on Food Metagroups; U.S. patent application Ser. No. 12/549,721, filed Aug. 28, 2009, entitled Processes and Systems Using and Producing Food Healthfulness Data based on Linear Combinations of Nutrients; and US patent application Ser. No. 12/549,958, filed Aug. 28, 2009, entitled Processes and Systems for Achieving and Assisting in Improved Nutrition, all of which are hereby incorporated herein by reference in their entireties.

FIELD OF THE INVENTION

Processes are provided for selecting, ingesting and/or purchasing foods for achieving weight control and/or healthful nutrition, as well as processes for producing food products, and systems for assisting with each of the foregoing.

BACKGROUND OF THE INVENTION

Weight Watchers International, Inc. is the world's leading provider of weight management services, operating globally through a network of Company-owned and franchise operations. Weight Watchers provides a wide range of products, publications and programs for those interested in weight loss and weight control. With over four decades of weight management experience, expertise and know-how, Weight Watchers has become one of the most recognized and trusted brand names among weight conscious consumers.

Years ago, Weight Watchers pioneered innovative and successful methods for weight control and systems for assisting consumers in practicing such methods. Such methods and systems are the subjects of U.S. Pat. No. 6,040,531; U.S. Pat. No. 6,436,036; U.S. Pat. No. 6,663,564; U.S. Pat. No. 6,878,885 and U.S. Pat. No. 7,361,143, each of which is incorporated herein by reference in its entirety. These methods assign values to food servings based on their calorie content, which is increased on the basis of fat content and decreased on the basis of dietary fiber content. This assignment is carried out using a proprietary formula developed by Weight Watchers scientists. The values for food servings consumed each day are summed and the consumer ensures that they do not exceed a predetermined maximum value. These methods afford a simple and effective weight control framework, especially for those who cannot devote substantial attention to their weight control efforts.

While the existing Weight Watchers® program has provided consumers with effective techniques that have assisted millions in their efforts to lose excess body weight using its proprietary formula, consumers have long expressed a desire that the formula reflect the relative satiety of different foods. Unfortunately, until now it has not been possible to quantify the aspect of satiety so that it could be incorporated in such a formula.

While consumers are striving to control their body weight, whether for the object of losing or gaining weight, or simply to maintain the weight they have, they are also eager to ensure that they are eating healthfully. Both government and private entities are attempting to implement measures to educate consumers so that they might chose and consume healthier foods. In the United States of America (US), food products are required to display lists of ingredients and provide additional information such as the content of each macronutrient, total calories and content of nutrients such as sodium and saturated fat that are particularly important to those with cardiovascular diseases.

The Food Standards Agency of the United Kingdom has implemented a food labeling system termed the "Traffic Light Labeling" system that encourages food manufacturers to label their foods in a standard fashion to enable consumers to compare one product against another by comparing the amounts of four different nutrients in each, including fat, saturated fat or "saturates", sugar and salt, and, in some cases, calorie content. For each nutrient, and the calorie content (if displayed), a color code is provided to indicate whether the amount of that nutrient is "high" (red color code), "medium" (amber color code) or "low" (green color code). For those keeping track of one or more particular nutrients, such as sodium and saturated fat in the case of those with a cardiovascular condition, this labeling system can be quite effective. But for those trying to develop an overall sense of the healthfulness of each food product they are considering for purchase and/or consumption, a considerable amount of judgment may be necessary to determine whether to purchase or consume a particular food product.

Published PCT application WO 98/45766 to Sanchez proposes a food group nutritional value calculator that inputs data such as that displayed in following the Traffic Light Labeling system along with a consumer's selection of one of eight "food groups". Based on the food group selection, the calculator carries out a corresponding decision-tree algorithm by comparing the input amounts of selected nutrients against standard values specific to each of the separate food groups. Based on one or more such comparisons, the food is classified as either "Excellent", "Very Good", "Good" or "Avoid".

DISCLOSURE

FIGS. 1-9 are tables of data used in processes disclosed herein for producing data representing the relative healthfulness of various foods;

Figure 10:
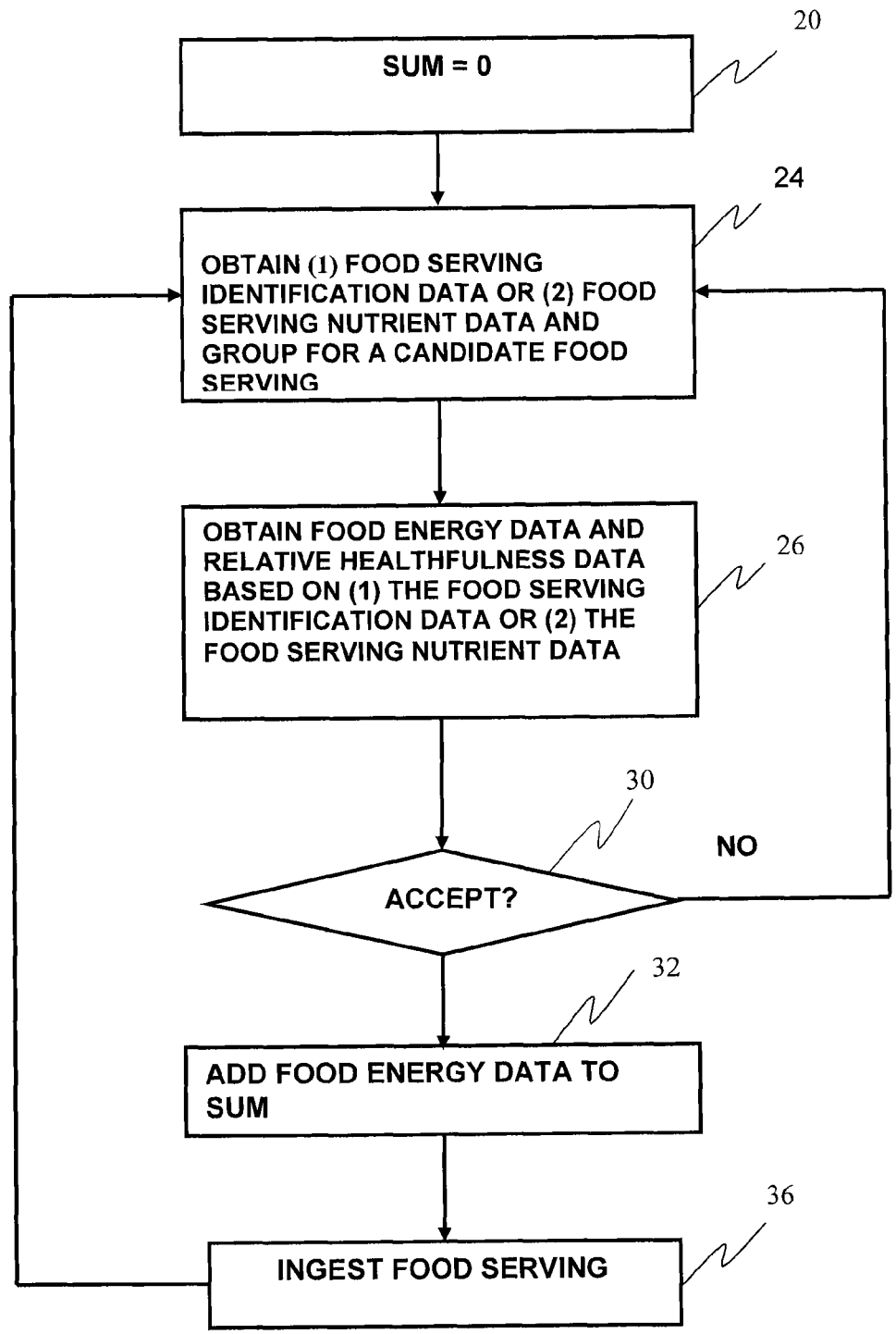
FIG. 10 is a flow chart illustrating a process for controlling body weight in a human being in accordance with certain embodiments.

For this application the following terms and definitions shall apply:

The term "energy content" as used herein refers to the energy content of a given food, whether or not adjusted for the metabolic conversion efficiency of one or more nutrients in the food.

The term "metabolic conversion efficiency" as used herein includes both absolute measures of metabolic conversion efficiency and the metabolic conversion efficiency of nutrients relative to each other.

The term "data" as used herein means any indicia, signals, marks, symbols, domains, symbol sets, representations, and any other physical form or forms representing information, whether permanent or temporary, whether visible, audible, acoustic, electric, magnetic, electromagnetic or otherwise manifested. The term "data" as used to represent predetermined information in one physical form shall be deemed to encompass any and all representations of corresponding information in a different physical form or forms.

The term "presentation data" as used herein means data to be presented to a user in any perceptible form, including but not limited to, visual form and aural form. Examples of presentation data include data displayed on a visual presentation device, such as a monitor, and data printed on paper.

The term "presentation device" as used herein means a device or devices capable of presenting data to a user in any perceptible form.

The term "database" as used herein means an organized body of related data, regardless of the manner in which the data or the organized body thereof is represented. For example, the organized body of related data may be in the form of one or more of a table, a map, a grid, a packet, a datagram, a frame, a file, an e-mail, a message, a document, a list or in any other form.

The term "image dataset" as used herein means a database suitable for use as presentation data or for use in producing presentation data.

The term "auxiliary image feature" as used herein means one or more of the color, brightness, shading, shape or texture of an image.

The term "network" as used herein includes both networks and internetworks of all kinds, including the Internet, and is not limited to any particular network or inter-network. For example, "network" includes those that are implemented using wired links, wireless links or any combination of wired and wireless links.

The terms "first", "second", "primary" and "secondary" are used to distinguish one element, set, data, object, step, process, activity or thing from another, and are not used to designate relative position or arrangement in time, unless otherwise stated explicitly.

The terms "coupled", "coupled to", and "coupled with" as used herein each mean a relationship between or among two or more devices, apparatus, files, circuits, elements, functions, operations, processes, programs, media, components, networks, systems, subsystems, and/or means, constituting any one or more of (a) a connection, whether direct or through one or more other devices, apparatus, files, circuits, elements, functions, operations, processes, programs, media, components, networks, systems, subsystems, or means, (b) a communication relationship, whether direct or through one or more other devices, apparatus, files, circuits, elements, functions, operations, processes, programs, media, components, networks, systems, subsystems, or means, and/or (c) a functional relationship in which the operation of any one or more devices, apparatus, files, circuits, elements, functions, operations, processes, programs, media, components, networks, systems, subsystems, or means depends, in whole or in part, on the operation of any one or more others thereof.

The terms "communicate," "communicating" and "communication" as used herein include both conveying data from a source to a destination, and delivering data to a communication medium, system, channel, network, device, wire, cable, fiber, circuit and/or link to be conveyed to a destination. The term "communications" as used herein includes one or more of a communication medium, system, channel, network, device, wire, cable, fiber, circuit and link.

The term "processor" as used herein means processing devices, apparatus, programs, circuits, components, systems and subsystems, whether implemented in hardware, software or both, and whether or not programmable. The term "processor" as used herein includes, but is not limited to one or more computers, hardwired circuits, neural networks, signal modifying devices and systems, devices and machines for controlling systems, central processing units, programmable devices and systems, field programmable gate arrays, application specific integrated circuits, systems on a chip, systems comprised of discrete elements and/or circuits, state machines, virtual machines, data processors, processing facilities and combinations of any of the foregoing.

The term "data processing system" as used herein means a system implemented at least in part by hardware and comprising a data input device, a data output device and a processor coupled with the data input device to receive data therefrom and coupled with the output device to provide processed data thereto.

The terms "obtain", "obtained" and "obtaining", as used with respect to a processor or data processing system mean (a) producing data by processing data, (b) retrieving data from storage, or (c) requesting and receiving data from a further data processing system.

The terms "storage" and "data storage" as used herein mean one or more data storage devices, apparatus, programs, circuits, components, systems, subsystems, locations and storage media serving to retain data, whether on a temporary or permanent basis, and to provide such retained data.

The terms "food serving identification data" and "food serving ID data" as used herein mean data of any kind that is sufficient to identify a food and to convey an amount thereof, whether by mass, weight, volume, or size, or by reference to a standard or otherwise defined food serving, or by amounts of constituents thereof. The terms "amount" and "amounts" as used herein refer both to absolute and relative measures.

The terms "food identification data" and "food ID data" as used herein mean data of any kind that is sufficient to identify a food, whether or not such data conveys an amount thereof.

A process for controlling body weight of a consumer comprises, for each of a plurality of candidate food servings, supplying at least one of respective food serving identification data and respective food serving nutrient data; obtaining respective food energy data representing an energy content of each of the candidate food servings and respective healthfulness data representing a relative healthfulness of each of the candidate food servings based on its at least one of respective food serving identification data and respective food serving nutrient data; selecting food servings from the plurality of candidate food servings based on its respective healthfulness data and its respective food energy data such that a sum of respective food energy data of the selected food servings bears a predetermined relationship to a predetermined food energy benchmark for the consumer in a given period; and ingesting the selected food servings.

In certain embodiments, meal plan data comprising data identifying candidate food servings to be ingested by the consumer over the given period is obtained based on the respective healthfulness data, the respective food energy data and the food energy benchmark, and the candidate food servings are ingested by the consumer in accordance with the meal plan data.

In certain embodiments, the respective healthfulness data for at least one of the candidate food servings is based on (a) a selected respective procedure for processing nutritional data of foods in a respective food group comprising the at least one of the candidate food servings, the respective food group being one of a plurality of food groups of a respective metagroup of a plurality of metagroups, each of the metagroups comprising a plurality of food groups and having a different respective procedure for processing the nutritional data of foods in the food groups within such metagroup, and (b) selected respective comparison data for the corresponding food group, at least some of the food groups in each metagroup having different respective comparison data than the other food groups in such metagroup. In certain embodiments, the respective healthfulness data representing a relative healthfulness of each of the candidate food servings is based on a linear combination of selected nutrient amounts present therein.

In certain embodiments, the respective food energy data representing an energy content of each of the candidate food servings is based on a human being's metabolic efficiency in utilizing first and second nutrients therein as energy. In certain embodiments, the respective food energy data representing an energy content of each of the candidate food servings is based on an energy contribution of each of its protein content, its carbohydrate content, its dietary fiber content and its fat content.

A process for selecting and purchasing food comprises, using at least one of food identification data and food serving nutrient data of a food offered for sale, obtaining food energy data representing an energy content thereof and relative healthfulness data representing a relative healthfulness thereof; selecting the food offered for sale based on its food energy data and its relative healthfulness data; and purchasing the selected food offered for sale.

In certain embodiments, the relative healthfulness data of the food offered for sale is based on (a) a selected respective procedure for processing nutritional data of foods in a respective food group comprising the food offered for sale, the respective food group being one of a plurality of food groups of a respective metagroup of a plurality of metagroups, each of the metagroups comprising a plurality of food groups and having a different respective procedure for processing the nutritional data of foods in the food groups within such metagroup, and (b) selected respective comparison data for the corresponding food group, at least some of the food groups in each metagroup having different respective comparison data than the other food groups in such metagroup. In certain embodiments, the relative healthfulness data of the food offered for sale is based on a linear combination of selected nutrient amounts present therein.

In certain embodiments, the food energy data representing an energy content of the food offered for sale is based on a human being's metabolic efficiency in utilizing first and second nutrients therein as energy. In certain embodiments, the food energy data representing an energy content of the food offered for sale is based on an energy contribution of each of its protein content, its carbohydrate content, its dietary fiber content and its fat content.

A process for providing data to a consumer to assist in a process for controlling the consumer's weight comprises receiving in a data processing system data provided by a consumer for a food serving selected by the consumer including at least one of food serving identification data and food serving nutrient data; using a processor of the data processing system, obtaining food energy data and food healthfulness data based on the at least one of food serving identification data and food serving nutrient data; and at least one of (a) communicating the food energy data and the food healthfulness data to a device for presentation to the consumer, and (b) presenting the food energy data and the food healthfulness data to the consumer via a presentation device of the data processing system.

In certain embodiments, the food healthfulness data is based on (a) a selected respective procedure for processing nutritional data of foods in a respective food group comprising the food serving, the respective food group being one of a plurality of food groups of a respective metagroup of a plurality of metagroups, each of the metagroups comprising a plurality of food groups and having a different respective procedure for processing the nutritional data of foods in the food groups within such metagroup, and (b) selected respective comparison data for the corresponding food group, at least some of the food groups in each metagroup having different respective comparison data than other food groups in such metagroup. In certain embodiments, the food healthfulness data is based on a linear combination of selected nutrient amounts present in the food serving.

In certain embodiments, the respective food energy data is based on a human being's metabolic efficiency in utilizing first and second nutrients in the food serving as energy. In certain embodiments, the respective food energy data of the food serving is based on an energy contribution of each of its protein content, its carbohydrate content, its dietary fiber content and its fat content.

A system for providing data to a consumer to assist in a process for controlling the consumer's weight comprises an input operative to receive data provided by a consumer for a food serving selected by the consumer including at least one of food serving identification data and food serving nutrient data; a processor coupled with the input to receive the data provided by the consumer and configured to obtain food energy data and food healthfulness data based on the at least one of food serving identification data and food serving nutrient data; and at least one of (a) communications coupled with the processor to receive the food energy data and the food healthfulness data therefrom and to communicate the food energy data and the food healthfulness data to a device for presentation to the consumer, and (b) a presentation device coupled with the processor to receive the food energy data and the food healthfulness data and operative to present the food energy data and the food healthfulness data to the consumer.

In certain embodiments, the processor is configured to obtain the food healthfulness data based on (a) a selected respective procedure for processing nutritional data of foods in a respective food group comprising the food serving, the respective food group being one of a plurality of food groups of a respective metagroup of a plurality of metagroups, each of the metagroups comprising a plurality of food groups and having a different respective procedure for processing the nutritional data of foods in the food groups within such metagroup, and (b) selected respective comparison data for the corresponding food group, at least some of the food groups in each metagroup having different respective comparison data than the other food groups in such metagroup. In certain embodiments, the processor is configured to obtain the food healthfulness data based on a linear combination of selected nutrient amounts present in the food serving.

In certain embodiments, the processor is configured to obtain the food energy data based on a human being's metabolic efficiency in utilizing first and second nutrients in the food serving as energy. In certain embodiments, the processor is configured to obtain the food energy data of the food serving based on an energy contribution of each of its protein content, its carbohydrate content, its dietary fiber content and its fat content.

A process for providing meal plan data to a consumer, comprises receiving request data in a data processing system representing a request for a meal plan from a consumer; in response to the request, obtaining meal plan data in the data processing system representing a plurality of predetermined food servings to be consumed by the consumer during a predetermined period based on food energy data and relative healthfulness data for each thereof; and at least one of (a) communicating the meal plan data to a device for presentation to the data requester, and (b) presenting the meal plan data to the data requester via a presentation device of the data processing system.

In certain embodiments, the food energy data of at least one of the plurality of predetermined food servings is based on a human being's metabolic efficiency in utilizing first and second nutrients therein as energy. In certain embodiments, the food energy data of at least one of the plurality of predetermined food servings is based on an energy contribution of each of its protein content, its carbohydrate content, its dietary fiber content and its fat content.

In certain embodiments, the relative healthfulness data of at least one of the plurality of predetermined food servings is based on (a) a selected respective procedure for processing nutritional data of foods in a respective food group comprising the at least one of the plurality of predetermined food servings, the respective food group being one of a plurality of food groups of a respective metagroup of a plurality of metagroups, each of the metagroups comprising a plurality of food groups and having a different respective procedure for processing the nutritional data of foods in the food groups within such metagroup, and (b) selected respective comparison data for the corresponding food group, at least some of the food groups in each metagroup having different respective comparison data than other food groups in such metagroup. In certain embodiments, the relative healthfulness data of at least one of the plurality of predetermined food servings is based on a linear combination of selected nutrient amounts present in the at least one of the plurality of predetermined food servings.

A system for providing meal plan data to a consumer comprises an input operative to receive request data representing a request for a meal plan from the consumer; a processor coupled with the input to receive the request data and configured to obtain meal plan data representing a plurality of predetermined food servings to be consumed by the consumer during a predetermined period based on food energy data and relative healthfulness data therefor; and at least one of (a) communications coupled with the processor to receive the meal plan data therefrom and to communicate the meal plan data to a device for presentation to the consumer, and (b) a presentation device coupled with the processor to receive the meal plan data and operative to present the meal plan data to the consumer.

In certain embodiments, the processor is configured to obtain the relative healthfulness data of at least one of the plurality of predetermined food servings based on (a) a selected respective procedure for processing nutritional data of foods in a respective food group comprising the at least one of the plurality of predetermined food servings, the respective food group being one of a plurality of food groups of a respective metagroup of a plurality of metagroups, each of the metagroups comprising a plurality of food groups and having a different respective procedure for processing the nutritional data of foods in the food groups within such metagroup, and (b) selected respective comparison data for the corresponding food group, at least some of the food groups in each metagroup having different respective comparison data than other food groups in such metagroup. In certain embodiments, the processor is configured to obtain the relative healthfulness data of at least one of the plurality of predetermined food servings based on a linear combination of selected nutrient amounts present therein.

In certain embodiments, the processor is configured to obtain the food energy data of at least one of the plurality of predetermined food servings based on a human being's metabolic efficiency in utilizing first and second nutrients therein. In certain embodiments, the processor is configured to obtain the food energy data of at least one of the plurality of predetermined food servings based on an energy contribution of each of its protein content, its carbohydrate content, its dietary fiber content and its fat content.

A process for producing a food product having food energy data and relative healthfulness data associated therewith comprises, obtaining a food product, supplying at least one of food identification data and food nutrient data of the food product; obtaining food energy data and relative healthfulness data for the food product based on the at least one of food identification data and food nutrient data of the food product; and associating the food energy data and the relative healthfulness data with the food product.

In certain embodiments, the food energy data and the relative healthfulness data is associated with the food product by including the food energy data and the relative healthfulness data on a substrate associated with the food product. In certain ones of such embodiments, the substrate comprises a package for the food product. In certain ones of such embodiments, the substrate comprises a label accompanying the food product.

Food servings can be specified in various ways, and preferably in ways that are meaningful to consumers according to their local dining customs. Food servings may be specified by weight, mass, size or volume, or according to customary ways of consuming food in the relevant culture. For example, in the United States it is customary to use measures such as cups, quarts, teaspoons, tablespoons, ounces, pounds, or even a "pinch", in Europe, it is more common to use units such as liters, deciliters, grams and kilograms. In China and Japan it is also appropriate to use a measure such as a standard mass or weight held by chopsticks when consuming food.

In certain embodiments, food energy data is produced based on protein energy data representing the protein energy content, carbohydrate energy data representing the carbohydrate energy content and fat energy data representing the fat energy content, of a candidate food serving, by applying respective weight data to weight each of the protein energy data, the carbohydrate energy data and the fat energy data, each of the weight data representing the relative metabolic conversion efficiency of the corresponding nutrient and forming the food energy data based on a sum of the weighted protein energy data, the weighted carbohydrate energy data and the weighted fat energy data. The data for the various nutrients is provided either by the consumer or by another source based on data from the consumer, such as food identification data. If the protein energy data is represented as "PRO", the carbohydrate energy data as "CHO" and the fat energy data as "FAT", in certain ones of such embodiments, the food energy data (represented as "FED") is obtained by processing the data in the manner represented by the following equation:

$$FED=(W\text{pro}\times PRO)+(W\text{cho}\times CHO)+(W\text{fat}\times FAT), \quad (1)$$

where Wpro represents the respective weighting data for PRO, Wcho represents the respective weighting data for CHO and Wfat represents the respective weighting data for FAT. In certain ones of such embodiments, Wpro is selected from the range $0.7 \leq W\text{pro} \leq 0.8$, Wcho is selected from the range $0.9 \leq W\text{cho} \leq 0.95$ and Wfat is selected from the range $0.97 \leq W\text{fat} \leq 1.0$. In certain ones of such embodiments, Wpro is substantially equal to 0.8, Wcho is substantially equal to 0.95 and Wfat is substantially equal to 1.0. Various measures of energy can be employed, such as kilocalories (kcal) and kilojoules (kJ).

In certain embodiments, food energy data is produced based on protein data representing the mass or weight of the protein content (represented as PROm), carbohydrate data representing the mass or weight of the carbohydrate content (represented as CHOm) and fat data representing the mass or weight of the fat content (represented as FATm), of a candidate food serving. In such embodiments, the protein data, carbohydrate data and fat data are converted to energy data in producing the food energy data, by processing the protein data, carbohydrate data and fat data in the manner represented by the following equation:

$$FED=(W\text{pro}\times Cp\times PROm)+(W\text{cho}\times Cc\times CHOm)+ \\ (W\text{fat}\times Cf\times FATm), \quad (2)$$

where Cp is a conversion factor for converting PROm to data representing the energy content of PROm, Cc is a conversion factor for converting CHOm to data representing the energy content of CHOm, and Cf is a conversion factor for converting FATm to data representing the energy content of FATm. For example where the food energy data is represented in kilocalories and PROm, CHOm and FATm are expressed in grams, Cp is selected as 4 kilocalories/gram, Cc is selected as 4 kilocalories/gram and Cf is selected as 9 kilocalories/gram. Mass and weight data can be expressed in the alternative by units such as ounces and pounds.

In certain embodiments, food energy data is produced based on total food energy data representing the total energy content, protein energy data representing the protein energy content, and dietary fiber energy data representing the dietary fiber energy content, of a candidate food serving. More specifically, the food energy data is produced by separating data representing the protein energy content and the dietary fiber energy content (if present) from the total food energy data to produce reduced energy content data, applying respective weight data to weight each of the protein energy data and the dietary fiber energy data, each of the weight data representing the relative metabolic conversion efficiency of the corresponding nutrient and forming the food energy data based on a sum of the reduced energy content data, the weighted protein energy data, and the weighted dietary fiber energy data. The data for the various nutrients is provided either by the consumer or by another source based on data from the consumer, such as food identification data. If the total food energy data is represented as "TFE", protein energy data is represented as "PRO" and the dietary fiber energy data as "DF", in certain ones of such embodiments where TFE includes an energy component of DF (as in the case of foods labeled according to practices adopted in the US and in the Dominion of Canada (CA)), the food energy data is obtained by processing the data in the manner represented by the following equation:

$$FED=(TFE-PRO-DF)+(W\text{pro}\times PRO)+(Wdf\times DF), \quad (3)$$

where Wpro represents the respective weighting data for PRO and Wdf represents the respective weighting data for DF. In certain ones of such embodiments, Wpro is selected from the range $0.7 \leq W\text{pro} \leq 0.8$ and Wdf is selected from the range $0 < Wdf \leq 0.5$. In certain ones of such embodiments, Wpro is substantially equal to 0.8 and Wdf is substantially equal to 0.25. Various measures of energy can be employed, such as kilocalories (kcal) and kilojoules (kJ).

For those instances where TFE does not include a dietary fiber component (as in the case of foods labeled according to practices adopted in Australia (AU) and the countries of central Europe (CE)), the process of equation (3) is modified to the following form:

$$FED=(TFE-PRO)+(W\text{pro}\times PRO)+(Wdf\times DF). \quad (4)$$

In certain embodiments, food energy data is produced based both on the total food energy data, as well as on protein data representing the mass or weight of the protein content (represented as PROm) and dietary fiber data representing the mass or weight of the dietary fiber content (represented as DFm), of a candidate food serving. In such embodiments and for foods labeled as in the US and CA, the protein data and dietary fiber data are converted to energy data in producing the food energy data, by processing the total food energy data, the protein data and dietary fiber data in the manner represented by the following equation:

$$FED=[TFE-(Cp\times PROm)-(Cdf\times DFm)]+(W\text{pro}\times Cp\times \\ PROm)+(Wdf\times Cdf\times DFm), \quad (5)$$

where Cp is a conversion factor for converting PROm to data representing the energy content of PROm and Cdf is a conversion factor for converting DFm to data representing an energy content of DFm. For example where the food energy data is represented in kilocalories and PROm and DFm are expressed in grams, Cp is selected as 4 kilocalories/gram and Cdf is selected as 4 kilocalories/gram. Mass and weight data can be expressed in the alternative by units such as ounces and pounds.

For those instances where TFE does not include a dietary fiber component (as in the case of foods labeled according to practices adopted in AU and CE), the process of equation (5) is modified to the following form:

$$FED=[TFE-(Cp\times PROm)]+(W\text{pro}\times Cp\times PROm)+(Wdf\times \\ Cdf\times DFm). \quad (6)$$

In certain embodiments, food energy data is produced based on protein data representing the protein energy content of a candidate food serving, carbohydrate data representing its carbohydrate energy content, fat data representing its fat energy content, and dietary fiber data representing its dietary fiber energy content. This data is provided either by the consumer or from another source based on data from the consumer, such as food identification data. If the protein energy data is represented as "PRO", the carbohydrate energy data as "CHO", the fat energy data as "FAT", and the dietary fiber energy data as "DF", in certain ones of such embodiments, the food energy data (represented as "FED") is obtained by processing the data in the manner represented by the following equation:

$$FED = PRO + CHO + FAT + DF. \tag{7}$$

In certain ones of such embodiments, food energy data is produced based on the protein energy data, the carbohydrate energy data, the fat energy data, and the dietary fiber energy data, of the candidate food serving, by applying respective weight data to weight each of the protein energy data, the carbohydrate energy data, the fat energy data and the dietary fiber energy data representing its relative metabolic conversion efficiency and forming the food energy data based on a sum of the weighted protein energy data, the weighted carbohydrate energy data, the weighted fat energy data and the weighted dietary fiber energy data. If Wpro represents the respective weighting data for PRO, Wcho represents the respective weighting data for CHO, Wfat represents the respective weighting data for FAT and Wdf represents the respective weighting data for dietary fiber, in certain ones of such embodiments, the food energy data (represented as "FED") is obtained by processing the data in the manner represented by the following equation:

$$FED = (Wpro \times PRO) + (Wcho \times CHO) + (Wfat \times FAT) + (Wdf \times DF). \tag{8}$$

In certain ones of such embodiments, Wpro is selected from the range $0.7 \leq Wpro \leq 0.8$, Wcho is selected from the range $0.9 \leq Wcho \leq 0.95$, Wfat is selected from the range $0.97 \leq Wfat \leq 1.0$ and Wdf is selected from the range $0 < Wdf \leq 0.5$ In certain ones of such embodiments, Wpro is substantially equal to 0.8, Wcho is substantially equal to 0.95, Wfat is substantially equal to 1.0 and Wdf is substantially equal to 0.25.

In certain embodiments, food energy data is produced based on protein data representing the mass or weight of the protein content (represented as PROm), carbohydrate data representing the mass or weight of the carbohydrate content (represented as CHOm), fat data representing the mass or weight of the fat content (represented as FATm) and dietary fiber data representing the mass or weight of the dietary fiber content (represented as DFm), of a candidate food serving. In such embodiments, the protein data, carbohydrate data, fat data and dietary fiber data, are converted to energy data in producing the food energy data, by processing the protein data, carbohydrate data, fat data and dietary fiber data in the manner represented by the following equation:

$$FED = (Wpro \times Cp \times PROm) + (Wcho \times Cc \times CHOm) + (Wfat \times Cf \times FATm) + (Wdf \times Cdf \times DFm), \tag{9}$$

where Cp is a conversion factor for converting PROm to data representing an energy content of PROm, Cc is a conversion factor for converting CHOm to data representing an energy content of CHOm, Cf is a conversion factor for converting FATm to data representing an energy content of FATm and Cdf is a conversion factor for converting DFm to data representing an energy content of DFm. For example where the food energy data is represented in kilocalories and PROm, CHOm, FATm and DFm are expressed in grams, Cp is selected as 4 kilocalories/gram, Cc is selected as 4 kilocalories/gram, Cf is selected as 9 kilocalories/gram and Cdf is selected as 4 kilocalories/gram.

In the US and in CA, where food labeling standards include a food product's dietary fiber in its total carbohydrate amount in grams (represented as "Total_CHOm" herein), food energy data may instead be produced by processing the protein data, carbohydrate data, fat data and dietary fiber data in the manner represented by the following equation:

$$FED = (Wpro \times Cp \times PROm) + (Wcho \times Cc \times [Total\_CHOm - DFm]) + (Wfat \times Cf \times FATm) + (Wdf \times Cdf \times DFm). \tag{10}$$

In certain embodiments, the food energy data is produced in a modified fashion in order to discourage consumption of foods having a high saturated fat content, so that the food energy data (FED) is based both on the relative metabolic conversion efficiency of selected nutrients and weighting data that promotes consumption of relatively more healthful foods. In such embodiments, and where (as in the US and CA) food labeling standards include a food product's saturated fat (represented as "Sat_FATm" herein) in its total amount of fat in grams (represented as "Total_FATm" herein), the food energy data is produced by processing the protein data, carbohydrate data, fat data, saturated fat data and dietary fiber data in the manner represented by the following equation:

$$FED = (Wpro \times Cp \times PROm) + (Wcho \times Cc \times [Total\_CHOm - DFm]) + (Wdf \times Cdf \times DFm) + (Wfat \times Cf \times [Total\_FATm - Sat\_FATm]) + (Wsfat \times Cf \times Sat\_Fatm), \tag{11}$$

wherein Wsfat represents modified weighting data for Sat_FATm. In certain ones of such embodiments, Wpro is selected from the range $0.7 \leq Wpro \leq 0.8$, Wcho is selected from the range $0.9 \leq Wcho \leq 0.95$, Wfat is selected from the range $0.97 \leq Wfat \leq 1.0$, Wdf is selected from the range $0 < Wdf \leq 0.5$, and Wsfat is selected from the range $1.0 \leq Wsfat \leq 1.3$. In particular ones of such embodiments, Wpro is substantially equal to 0.8, Wcho is substantially equal to 0.95, Wfat is substantially equal to 1.0, Wdf is substantially equal to 0.25 and Wsfat is substantially equal to 1.3.

The relatively higher value assigned to Wsfat is based, in part, on the desirability of discouraging consumption of saturated fat, due to the ill-health effects associated with this nutrient. The higher ranges and values of Wpro and Wcho in the presently disclosed embodiments relative to those employed in embodiments disclosed hereinabove, are useful for weight loss processes. That is, consumers engaged in a weight loss process by limiting their food energy consumption could, in some cases, be encouraged to eat foods higher in saturated fat if it is assigned a relatively higher weight than other nutrients, since this tends to reduce their overall food energy consumption. By assigning relatively higher ranges and values for Wpro and Wcho for use in processes that also weight saturated fat higher than unsaturated fat, the potential to encourage consumption of saturated fat is substantially reduced. Accordingly, the weights assigned to Wpro and Wcho in the presently disclosed embodiments are based both on the relative metabolic conversion efficiency of protein and carbohydrates and the desire to promote consumption of relatively more healthful foods.

In certain embodiments, for foods containing alcohol, the foregoing processes as represented by equation (11) are modified to add a term representing an energy component represented by the amount of alcohol in the food. Where the amount of alcohol (by weight or mass) is expressed in grams (represented as "ETOHm" herein), this term is produced by multiplying ETOHm by a weighting factor Wetoh and a conversion factor Cetoh, where Wetoh is selected from the range $1.0 \leq Wetoh \leq 1.3$, and in particular ones of such embodiments is substantially equal to 1.29, and Cetoh is selected as 9 kilocalories/gram, based on the principle that alcohol is metabolized in the same pathway as fat. The higher value assigned to Wetoh is based, in part, on the desirability of discouraging consumption of alcohol, due to the ill-health effects associated with this nutrient. Where a food contains alcohol, in certain embodiments its food energy data is produced by processing PROm, Total_CHOm, DFm, Total_FATm, Sat_FATm, and ETOHm in the manner represented by the following equation:

$$FED = (Wpro \times Cp \times PROm) + (Wcho \times Cc \times [Total\_CHOm - DFm]) + (Wdf \times Cdf \times DFm) + (Wfat \times Cf \times [Total\_FATm - Sat\_FATm]) + (Wsfat \times Cf \times Sat\_Fatm) + (Wetoh \times Cetoh \times ETOHm). \quad (12)$$

The process represented by equation (12) is modified for use in CE and AU and is represented as follows:

$$FED = (Wpro \times Cp \times PROm) + (Wcho \times Cc \times Total\_CHOm) + (Wdf \times Cdf \times DFm) + (Wfat \times Cf \times [Total\_FATm - Sat\_FATm]) + (Wsfat \times Cf \times Sat\_Fatm) + (Wetoh \times Cetoh \times ETOHm). \quad (13)$$

In certain embodiments, for foods containing sugar alcohol, the foregoing processes as represented by equations (12) and (13) are modified to add a term representing an energy component represented by the amount of sugar alcohol in the food. Where the amount of sugar alcohol (by weight or mass) is expressed in grams (represented as "SETOHm" herein), this term is produced by multiplying SETOHm by a weighting factor Wsetoh and a conversion factor Csetoh, where Wsetoh is selected from the range $0.9 \leq Wsetoh \leq 0.95$, and in particular ones of such embodiments is substantially equal to 0.95, and Csetoh is selected from the range 0.2 to 4.0 kilocalories/gram, and in particular ones of such embodiments is substantially equal to 2.4. Where a food contains sugar alcohol, in certain embodiments its food energy data is produced by processing PROm, Total_CHOm, DFm, Total_FATm, Sat_ FATm, ETOHm and SETOHm in the manner represented by the following equation:

$$FED = (Wpro \times Cp \times PROm) + (Wcho \times Cc \times [Total\_CHOm - DFm - SETOHm]) + (Wdf \times Cdf \times DFm) + (Wfat \times Cf \times [Total\_FATm - Sat\_FATm]) + (Wsfat \times Cf \times Sat\_Fatm) + (Wetoh \times Cetoh \times ETOHm) + (Wsetoh \times Csetoh \times SETOHm). \quad (14)$$

The process represented by equation (14) is modified for use in CE and AU and is represented as follows:

$$FED = (Wpro \times Cp \times PROm) + (Wcho \times Cc \times [Total\_CHOm - SETOHm]) + (Wdf \times Cdf \times DFm) + (Wfat \times Cf \times [Total\_FATm - Sat\_FATm]) + (Wsfat \times Cf \times Sat\_Fatm) + (Wetoh \times Cetoh \times ETOHm) + (Wsetoh \times Csetoh \times SETOHm). \quad (15)$$

For the consumer's convenience, in many applications (such as the Weight Watchers® program) the food energy data is converted to simplified whole number data for a candidate food serving by producing dietary data expressed as whole number data by dividing the food energy data by factor data, such as data having a value of 35, and rounding the resulting value to produce the simplified whole number data. (Of course, to assign 35 as the value of the factor data is arbitrary, and any other value such as 50, 60 or 70 may be used for this purpose.)

In the manner described above, the consumer can easily track food consumption throughout a period, such as a day or a week, (either manually or with the assistance of a data processing system) to ensure that a predetermined sum of the dietary data for the food consumed bears a predetermined relationship to a value of predetermined whole number benchmark data based on one or more of the consumer's age, body weight, height, gender and activity level. For example, if the consumer is following a weight loss program, the predetermined whole number benchmark data is set at a value selected to ensure that the consumer will lose weight at a safe rate if he or she consumes an amount of food during the period having a sum of dietary data that does not exceed the predetermined whole number benchmark data.

Since individual food energy needs vary with the individual's age, weight, gender, height and activity level, in certain embodiments the predetermined whole number benchmark data is selected based on one or more of these variables. In such embodiments, food energy needs are estimated based on methods published by the National Academies Press, Washington, D.C., USA in *Dietary Reference Intakes for Energy, Carbohydrates, Fiber, Fat, Fatty Acids, Cholesterol, Protein and Amino Acids*, 2005, pages 203 and 204. More specifically, as explained therein these methods estimate that men aged 19 years and older have a total energy expenditure (TEE) determined as follows:

$$TEE = 864 - (9.72 \times age) + PA \times (14.2 \times weight + 503 \times height), \quad (16)$$

and that women aged 19 years and older have a TEE determined as follows:

$$TEE = 387 - (7.31 \times age) + PA \times (10.9 \times weight + 660.7 \times height), \quad (17)$$

where age is given in years, weight in kilograms and height in meters.

In such embodiments, these methods are employed on the basis that all individuals have a "low active" activity level, so that the activity level (PA) for men is set at 1.12 and PA for women is set at 1.14. The published methods assume a 10 percent conversion cost regardless of the types and amounts of nutrients consumed; consequently, TEE is adjusted by subtracting 10 percent of the calculated TEE. Also, the published method of calculating TEE assigns an energy content of zero to certain foods having a non-zero energy content. The total energy content of such foods consumed within a given day generally falls within a range of 150 to 250 kilocalories, which may be normalized as 200 kilocalories. Accordingly, TEE as determined by the published method is adjusted to produce adjusted TEE (ATEE) in a process represented by the following equation:

$$ATEE = TEE - (TEE \times 0.10) + 200, \quad (18)$$

where ATEE and TEE are given in kilocalories.

For consumers carrying out a process of reducing body weight, the predetermined whole number benchmark is obtained by subtracting an amount from the adjusted TEE selected to ensure a predetermined weight loss over a predetermined period of time. For example, a safe weight loss process can be selected to produce a loss of two pounds per week, or a consumption of 1000 kilocalories per day less than ATEE for a given individual. In this example, to produce the predetermined whole number benchmark data (PWNB), where the factor data used to produce the dietary data for the candidate food servings (whether having a value of 35, 50, 60, 70 or other value) is represented as FAC, such data is produced by a process represented by the following equation:

$$PWNB = (ATEE - 1000) \div FAC. \quad (19)$$

To achieve weight loss, the value of (ATEE−1000) in certain embodiments is selected to fall within a range of 1000 kilocalories to 2500 kilocalories, so that if (ATEE−1000) is less than 1000 kilocalories, then (ATEE is set equal to 1000 kilocalories, and if (ATEE−1000) is greater than 2500 kilocalories, (ATEE−1000) is set equal to 2500 kilocalories. However, in various other embodiments, the upper limit of 2500 kilocalories varies from 2000 to 3000 kilocalories, and the lower limit of 1000 kilocalories varies from 500 to 1500 kilocalories.

In certain embodiments, the relative healthfulness data is determined in a manner that depends on a particular food group of the selected food. In certain ones of such embodiments, the healthfulness data is determined in a first, common manner for foods within a first metagroup comprising the following groups: beans, dry & legumes; and oils. The healthfulness data (HD) for these groups is obtained based on a linear combination of fat content data, saturated fat content data, sugar content data and sodium content data for the food. In one such embodiment, the healthfulness data is produced by processing fat content data (F_data), saturated fat content data (SF_data), sugar content data (S_data) and sodium content data (NA_data), as follows, wherein such data is determined as explained hereinbelow:

$$HD=[(2\times(SF\_data+F\_data)+S\_data+NA\_data]/4/\text{kcal}\_DV \quad (20)$$

where kcal_DV is determined as explained hereinbelow. The table of FIG. 1 illustrates how the foods in these groups are ranked according to their healthfulness based on their respective healthfulness data produced in accordance with the process represented by equation (20) and a comparison thereof against the exemplary comparison data included therein. These values may be varied from place to place, from culture to culture and from time to time, to provide a fair comparison of available foods and food products.

It will also be appreciated that the food groups and metagroups, and the corresponding procedures and comparison values, as disclosed herein may be varied based on variations in the foods and food products available from place to place, culture to culture and over time. They may also vary to accommodate the needs and desires of certain segments of the population, such as those with special needs (for example, diabetic patients and those living in extreme climates) and those with particular healthfulness goals (which can vary, for example, with physical activity level). Such groups, metagroups, procedures, and comparison values are selected based on the similarities of foods and the manner in which related foods vary in the amounts and types of nutrients that tend to affect their healthfulness.

The value selected for kcal_DV is selected to represent a daily calorie value that depends on the purposes or needs of the class of consumers for whom the relative healthfulness data is provided. For example, if this class encompasses individuals desiring to loose body weight, the value of kcal_DV is selected as a daily calorie target to ensure weight loss, such as 1500 kcal. However, this value may differ from culture to culture and from country to country. For example, the energy needs of those living in China are generally lower than those living in the United States, so that kcal_DV may be selected at a lower value for Chinese individuals trying to reduce body weight than for those living in the United States. As a further example, if the class of consumers for whom the relative healthfulness data is provided encompasses athletes attempting to maintain body weight during training, kcal_DV may be set at a much higher level than 1500 kcal. For most purposes, kcal_DV may be selected in a range from 1000 kcal to 3000 kcal.

The value of SF_data is determined relative to a recommended or otherwise standardized limit on an amount or proportion of saturated fat to be included in a person's daily food intake. The recommended or otherwise standardized amount or proportion of saturated fat to be consumed daily is based on the person's presumed total food energy intake daily, and a proportion thereof represented by saturated fat. In certain embodiments, for consumers desiring to lose body weight, as explained hereinabove, a total food energy intake of 1500 kcal is assumed (although the amount may vary in other embodiments). If, for example, a maximum desirable percentage of saturated fat consumed as a proportion of total daily energy intake is assumed to be seven percent, then the total number of calories in saturated fat that the person consumes daily on such a diet should be limited to about 105 kcal (of a total of 1500 kcal). Since fat contains about nine kcal per gram, the person's daily consumption of saturated fat in this example should be limited to about twelve grams. However, the recommended or standardized limit on the proportion or amount of saturated fat to be consumed may vary from one class of consumer to another, as well as from country to country and from culture to culture. SF_data is determined by comparison to such a standard. In this example, therefore, SF_data is determined as the ratio of (a) the mass of saturated fat in a standard amount of the food under evaluation, to (b) twelve grams. While a different procedure or other amounts or proportions may be employed in other embodiments to evaluate the saturated fat content of a food, it is desired to determine SF_data in a manner that is reasonably comparable to the ways in which F_data, S_data and NA_data are determined.

Similarly to SF_data, the value of F_data is determined relative to a recommended or otherwise standardized limit on the amount or proportion of total fat to be included in a person's daily food intake. In those embodiments in which it is presumed that a person consumes 1500 kcal daily and a recommended proportion or limit of thirty percent of energy consumption in the form of fat is adopted, this translates to fifty grams of total fat on a daily basis. In this example, therefore, and in particular for comparability to SF_data, F_data is determined as the ratio of (a) the mass of total fat in a standard amount of the food under evaluation, to (b) fifty grams. Of course, a different procedure or other amounts or proportions may be employed in other embodiments to evaluate the total fat content of a food.

In a similar manner, the value of S_data is determined relative to a recommended or otherwise standardized limit on the amount or proportion of sugar to be included in a person's daily food intake. In those embodiments in which it is presumed that a person consumes 1500 kcal daily and a recommended proportion or limit of ten percent of food energy intake in the form of sugar is adopted, this translates to thirty eight grams of sugar on a daily basis (at four kcal per gram of sugar). In this example, therefore, and in particular for comparability to SF_data and F_data, S_data is determined as the ratio of (a) the mass of sugar in a standard amount of the food under evaluation, to (b) thirty eight grams. Of course, a different procedure or other amounts or proportions may be employed in other embodiments to evaluate the sugar content of a food.

In a manner similar to those described above, the value of NA_data is determined relative to a recommended or otherwise standardized limit on the amount or proportion of sodium to be included in a person's daily food intake. In those embodiments in which a recommended limit of 2400 mg of sodium consumed daily is adopted, NA_data is determined as the ratio of (a) the mass of sodium in a standard amount of the food under evaluation, to (b) 2400 mg. Of course, a different procedure or other amounts or proportions may be employed in other embodiments to evaluate the sodium content of a food.

In such embodiments, the healthfulness data is determined in a second, common manner for foods within a second metagroup comprising the following groups: beef (cooked), cookies, cream & creamers, eggs, frankfurters, game (raw), game (cooked), lamb (cooked), luncheon meats, pizza, pork (raw), pork (cooked), sausage, snacks—pretzels, veal (raw) and veal (cooked). The healthfulness data (HD) for these groups is obtained based on a linear combination of the food's fat content data, saturated fat content data, sugar content data, sodium content data and energy density data. In one such embodiment, the healthfulness data is produced by processing F_data, SF_data, S_data, NA_data and ED_data of the food, as follows, wherein F_data, SF_data, S_data and NA_data are obtained as explained hereinabove:

$$HD = ED\_data + ([(2 \times SF\_data) + (2 \times F\_data) + NA\_data + S\_data] \times 100 / M\_serving), \quad (21)$$

where M_serving is the mass or weight of a standard serving of the food. In this particular embodiment, ED_data is obtained as the energy content of the food (in kcal) divided by its mass (in grams). The tables of FIGS. 1A and 1B illustrate how the foods in these groups are ranked according to their healthfulness based on their respective healthfulness data produced in accordance with the process represented by equation (21) and a comparison thereof against the exemplary comparison data included therein.

In such embodiments, the healthfulness data is determined in a third, common manner for foods within a third metagroup comprising the following groups: beverages; alcoholic beverages; sweet spreads—jams, syrups, toppings & nut butters. The healthfulness data (HD) for these groups is obtained based on a linear combination of the food's fat content data, saturated fat content data, sugar content data, sodium content data and energy density data. In one such embodiment, the healthfulness data is produced by processing F_data, SF_data, S_data, NA_data, ED_data and M_serving, as follows:

$$HD = (ED\_data \div 3) + [(2 \times SF\_data) + (2 \times F\_data) + (2 \times S\_data) + NA\_data] \div M\_serving. \quad (22)$$

The table of FIG. 2 illustrates how the foods in these groups are ranked according to their healthfulness based on their respective healthfulness data produced in accordance with the process represented by equation (22) and a comparison thereof against the exemplary comparison data included therein.

In such embodiments, the healthfulness data is determined in a fourth, common manner for foods within a fourth metagroup comprising the following groups: cheese, dairy & non-dairy, hard; and cheese, cottage & cream. The healthfulness data (HD) for these groups is obtained based on a linear combination of the food's fat content data, saturated fat content data, sugar content data, sodium content data and energy density data. In one such embodiment, the healthfulness data is produced by processing F_data, SF_data, S_data, NA_data, ED_data and M_serving, as follows:

$$HD = ED\_data + [(4 \times SF\_data) + (4 \times F\_data) + S\_data + NA\_data] \times 100 / M\_serving. \quad (23)$$

The table of FIG. 2A illustrates how the foods in these groups are ranked according to their healthfulness based on their respective healthfulness data produced in accordance with the process represented by equation (23) and a comparison thereof against the exemplary comparison data included in FIG. 2A.

In such embodiments, the healthfulness data is determined in a fifth, common manner for foods within a fifth metagroup comprising the following groups: breads; bagels; tortillas, wraps; breakfast—pancakes, waffles, pastries; and vegetable dishes The healthfulness data (HD) for these groups is obtained based on a linear combination of the food's fat content data, saturated fat content data, sugar content data, sodium content data and energy density data. In one such embodiment, the healthfulness data is produced by processing F_data, SF_data, S_data, NA_data, ED_data and M_serving, as follows:

$$HD = ED\_data + [(2 \times SF\_data) + F\_data + S\_data + (2 \times NA\_data) - DF\_data] \times 100 / M\_serving. \quad (24)$$

The value of DF_data is determined relative to a recommended or otherwise standardized minimum amount or proportion of dietary fiber to be included in a person's daily food intake. One such recommendation is that a minimum of ten grams of dietary fiber be consumed by a person for every 1000 kcal consumed daily. In those embodiments in which it is presumed that a person consumes 1500 kcal daily, this translates to a recommended minimum of fifteen grams of dietary fiber on a daily basis. Of course, a different procedure or other amounts or proportions may be employed in other embodiments to evaluate the recommended amount of dietary fiber to be consumed on a periodic basis. In this particular example, the value of DF_data is obtained as the ratio of the mass of dietary fiber in a standard serving of then food, to fifteen grams.

The table of FIG. 3 illustrates how the foods in these groups are ranked according to their healthfulness based on their respective healthfulness data produced in accordance with the process represented by equation (24) and a comparison thereof against the exemplary comparison data included in FIG. 3.

In such embodiments, the healthfulness data is determined in a sixth, common manner for foods within a sixth metagroup comprising the following groups: grains & pasta, cooked; and grains & pasta, uncooked. The healthfulness data (HD) for these groups is obtained based on a linear combination of the food's fat content data, saturated fat content data, sugar content data, sodium content data, energy density data and dietary fiber content data. In one such embodiment, the healthfulness data is produced by processing F_data, SF_data, S_data, NA_data, ED_data and DF_data, as follows:

$$HD = (ED\_data/3) + [([SF\_data + F\_data + (2 \times S\_data) + (2 \times NA\_data)]/4) - DF\_data] \times 100 / M\_serving. \quad (25)$$

The table of FIG. 3A illustrates how the foods of the groups in the sixth metagroup are ranked according to their healthfulness based on their respective healthfulness data produced in accordance with the process represented by equation (25) and a comparison thereof against the exemplary comparison data included in FIG. 3A.

In such embodiments, the healthfulness data is determined in a seventh, common manner for foods within a seventh metagroup comprising the following groups: breakfast cereals, hot, cooked; breakfast cereals, hot, uncooked; and fruit salads. The healthfulness data (HD) for these groups is obtained based on a linear combination of the food's saturated fat content data, fat content data, sugar content data, sodium content data and energy density data. In one such embodiment, the healthfulness data is produced by processing SF_data, F_data, S_data, NA_data and ED_data, as follows:

$$HD = ED\_data + [SF\_data + (2 \times F\_data) + (2 \times S\_data) + (2 \times NA\_data] \times 100 / M\_serving. \quad (26)$$

The table of FIG. 4 illustrates how the foods in these groups are ranked according to their healthfulness based on their respective healthfulness data produced in accordance with the process represented by equation (26) and a comparison thereof against the exemplary comparison data included in FIG. 4.

In such embodiments, the healthfulness data is determined in an eighth, common manner for foods within an eighth metagroup comprising the following groups: bars; cakes and pastries; and candy. The healthfulness data (HD) for these groups is obtained based on a linear combination of the food's fat content data, saturated fat content data, sodium content data, energy density data and sugar content data. In one such embodiment, the healthfulness data is produced by processing F_data, SF_data, NA_data, ED_data and S_data, as follows:

$$HD=ED\_data+[(2\times SF\_data)+F\_data+(2\times S\_data)+(2\times NA\_data)]\times 100/M\_serving. \quad (27)$$

The table of FIG. 5 illustrates how the foods in these groups are ranked according to their healthfulness based on their respective healthfulness data produced in accordance with the process represented by equation (27) and a comparison thereof against the exemplary comparison data included in FIG. 5.

In such embodiments, the healthfulness data is determined in a ninth, common manner for foods within a ninth metagroup comprising the following groups: dips; dressings; gravies; sauces; soups, condensed; soups, RTE; and spreads (other than sweet). The healthfulness data (HD) for these groups is obtained based on a linear combination of the food's fat content data, saturated fat content data, sodium content data, sugar content data and energy density data. In one such embodiment, the healthfulness data is produced by processing F_data, SF_data, S_data, NA_data, and ED_data, as follows:

$$HD=ED\_data+[(2\times SF\_data)+F\_data+S\_data+(2\times NA\_data)]\times 100/M\_serving. \quad (28)$$

The table of FIG. 6 illustrates how the foods in these groups are ranked according to their healthfulness based on their respective healthfulness data produced in accordance with the process represented by equation (28) and a comparison thereof against the exemplary comparison data included in FIG. 6.

In such embodiments, the healthfulness data is determined in a tenth, common manner for foods within a tenth metagroup comprising the following groups: beans, dry & legumes dishes; beef dishes; breakfast mixed dishes; cheese dishes; chili, stew; egg dishes; fish & shellfish dishes; lamb dishes; pasta dishes; pasta, cooked; pork dishes; poultry dishes; rice & grains dishes; salads, main course; salads, side; sandwiches; veal dishes and vegetarian meat substitutes. The healthfulness data (HD) for these groups is obtained based on a linear combination of the food's fat content data, saturated fat content data, sodium content data, sugar content data and energy density data. In one such embodiment, the healthfulness data is produced by processing F_data, SF_data, NA_data, S_data and ED_data, as follows:

$$HD=ED\_data+[(2\times SF\_data)+(2\times F\_data)+S\_data+(2\times NA\_data)]\times 100/M\_serving. \quad (29)$$

The tables of FIGS. 7 and 7A illustrate how the foods in these groups are ranked according to their healthfulness based on their respective healthfulness data produced in accordance with the process represented by equation (29) and a comparison thereof against the exemplary comparison data included in FIGS. 7 and 7A.

In such embodiments, the healthfulness data is determined in an eleventh, common manner for foods within an eleventh metagroup comprising the following groups: fruit—fresh, frozen & dried; and fruit & vegetable juices. The healthfulness data (HD) for these groups is obtained based on a linear combination of the food's sodium content data, sugar content data, saturated fat content data, fat content data and energy density data. In one such embodiment, the healthfulness data is produced by processing NA_data, S_data, SF_data, F_data and ED_data, as follows:

$$HD=ED\_data+[(2\times S\_data)+NA\_data+SF\_data+F\_data]\times 100/M\_serving. \quad (30)$$

The table of FIG. 8 illustrates how the foods in these groups are ranked according to their healthfulness based on their respective healthfulness data produced in accordance with the process represented by equation (30) and a comparison thereof against the exemplary comparison data included in FIG. 8.

In such embodiments, the healthfulness data is determined in a twelfth, common manner for foods within a twelfth metagroup comprising the following groups: vegetables, raw; and vegetables, cooked. The healthfulness data (HD) for these groups is obtained based on a linear combination of the food's sodium content data, sugar content data, saturated fat content data, fat content data and energy density data. In one such embodiment, the healthfulness data is produced by processing NA_data, S_data, SF_data, F_data and ED_data as follows:

$$HD=ED\_data+[S\_data+(1.5\times NA\_data)+(5\times SF\_data)+(5\times F\_data)]\times 100/M\_serving. \quad (31)$$

The table of FIG. 8A illustrates how the foods in these groups are ranked according to their healthfulness based on their respective healthfulness data produced in accordance with the process represented by equation (31) and a comparison thereof against the exemplary comparison data included in FIG. 8A.

In such embodiments, the healthfulness data is determined in a thirteenth, common manner for foods within a thirteenth metagroup comprising the following groups: gelatin, puddings; ice cream desserts; ice cream novelties; ice cream, sherbet, sorbet; sweet pies; and sweets—honey, sugar, syrup, toppings. The healthfulness data (HD) for these groups is obtained based on a linear combination of the food's sodium content data, fat content data, saturated fat content data, sugar content data, and energy density data. In one such embodiment, the healthfulness data is produced by processing NA_data, F_data, SF_data, S_data, and ED_data, as follows:

$$HD=ED\_data+[(2\times SF\_data)+F\_data+NA\_data+(2\times S\_data)]\times 100/M\_serving. \quad (32)$$

The table of FIG. 9 illustrates how the foods in these groups are ranked according to their healthfulness based on their respective healthfulness data produced in accordance with the process represented by equation (32) and a comparison thereof against the exemplary comparison data included in FIG. 9.

In such embodiments, the healthfulness data is determined in a fourteenth, common manner for foods within the following group: breakfast cereals, RTE. The healthfulness data (HD) for this group is obtained based on the saturated fat content data of the food, as well as its fat content data, sugar content data, sodium content data, dietary fiber content data and energy density data. In one such embodiment, the healthfulness data is produced by processing SF_data, F_data, S_data, NA_data, DF_data and ED_data, as follows:

$$HD=(ED\_data/3)+[(2\times S\_data)+SF\_data+F\_data+NA\_data-DF\_data]\times 100/M\_serving. \quad (33)$$

For this group, the most healthful foods have an HD value less than or equal to −0.36, while less healthful foods have an HD value greater than −0.36 and less than or equal to 1.66, even less healthful foods have an HD value greater than 1.66 and less than or equal to 2.91 and the most unhealthful foods have an HD value greater than 2.91.

In such embodiments, the healthfulness data is determined in a fifteenth, common manner for foods within an fifteenth metagroup comprising the following group: coffee/tea drinks with milk. The healthfulness data (HD) for this group is obtained based on the saturated fat content data, the fat content data, the sodium content data and the sugar content data of the food. In one such embodiment, the healthfulness data is produced by processing SF_data, F_data, S_data and NA_data, as follows:

$$HD=([(2\times SF\_data)+(2\times F\_data)+(2\times S\_data)+NA\_data]/4)/kcal\_DV. \quad (34)$$

For this group, the most healthful foods have an HD value less than or equal to 3.25, while relatively less healthful foods have an HD value greater that 3.25 and less than or equal to 3.471, even less healthful foods have an HD value greater than 3.471 and less than or equal to 4.18 and the least healthful foods have an HD value greater than 4.18.

In such embodiments, the healthfulness data is determined in a sixteenth, common manner for foods within the following group: crackers. The healthfulness data (HD) for this group is obtained based on the saturated fat content data, the fat content data, the sugar content data, the sodium content data and the energy density data of the food. In one such embodiment, the healthfulness data is produced by processing SF_data, F_data, S_data, NA_data and ED_data, as follows:

$$HD=(ED\_data/3)+[(2\times SF\_data)+F\_data+S\_data+(2\times NA\_data)]\times 100/M\_serving. \quad (35)$$

For this group, none of the foods are graded in the most healthful foods category, while relatively less healthful foods have an HD less than or equal to 1.805, even less healthful foods have an HD value greater than 1.805 and less than or equal to 3.2, and the least healthful foods have an HD value greater than 3.2.

In such embodiments, the healthfulness data is determined in a seventeenth, common manner for foods within the following group: fish, cooked. The healthfulness data (HD) for this group is obtained based on the saturated fat content data, the fat content data, the sugar content data, the sodium content data and the energy density data of the food. In one such embodiment, the healthfulness data is produced by processing SF_data, F_data, S_data, NA_data and ED_data, as follows:

$$HD=ED\_data+[(4\times SF\_data)+(4\times F\_data)+S\_data+(2\times NA\_data)]\times 100/M\_serving. \quad (36)$$

For this group, the most healthful foods have an HD value less than or equal to 3.2, while relatively less healthful foods have an HD value greater that 3.2 and less than or equal to 4.7, even less healthful foods have an HD value greater than 4.7 and less than or equal to 6.6, and the least healthful foods have an HD value greater than 6.6.

In such embodiments, the healthfulness data is determined in a eighteenth, common manner for foods within the following group: fruit, canned. The healthfulness data (HD) for this group is obtained based on the saturated fat content data, the fat content data, the sugar content data, the sodium content data and the energy density data of the food. In one such embodiment, the healthfulness data is produced by processing SF_data, F_data, S_data, NA_data and ED_data, as follows:

$$HD=ED\_data+[(2\times SF\_data)+(2\times F\_data)+(4\times S\_data)+(2\times NA\_data)]\times 100/M\_serving. \quad (37)$$

For this group, the most healthful foods have an HD value less than or equal to 1.56, while relatively less healthful foods have an HD value greater that 1.56 and less than or equal to 1.93, even less healthful foods have an HD value greater than 1.93 and less than or equal to 3.27, and the least healthful foods have an HD value greater than 3.27.

In such embodiments, the healthfulness data is determined in a nineteenth, common manner for foods within the following group: nuts, nut butters. The healthfulness data (HD) for this group is obtained based on the saturated fat content data, the fat content data, the sugar content data, the sodium content data and the energy density data of the food. In one such embodiment, the healthfulness data is produced by processing SF_data, F_data, S_data, NA_data and ED_data, as follows:

$$HD=(ED\_data/3)+[(2\times SF\_data)+F\_data+S\_data+NA\_data]\times 100/M\_serving. \quad (38)$$

For this group, none of the foods are graded within the most healthful foods category, while relatively less healthful foods have an HD value less than or equal to 1.5, even less healthful foods have an HD value greater than 1.5 and less than or equal to 5.6, and the least healthful foods have an HD value greater than 5.6.

In such embodiments, the healthfulness data is determined in a twentieth, common manner for foods within the following group: snacks, other. The healthfulness data (HD) for this group is obtained based on the saturated fat content data, the fat content data and the energy density data of the food. In one such embodiment, the healthfulness data is produced by processing SF_data, F_data and ED_data, as follows:

$$HD=ED\_data+[SF\_data+F\_data]\times 100/M\_serving. \quad (39)$$

For this group, none of the foods are graded within the most healthful foods category or in the relatively less healthful foods category, while even less healthful foods have an HD value less than or equal to 5.491, and the least healthful foods have an HD value greater than 5.491.

In such embodiments, the healthfulness data is determined in a twenty-first, common manner for foods within the following group: snacks—popcorn. The healthfulness data (HD) for this group is obtained based on the saturated fat content data of the food, as well as its fat content data, sugar content data, sodium content data, dietary fiber content data and energy density data. In one such embodiment, the healthfulness data is produced by processing SF_data, F_data, S_data, NA_data, DF_data and ED_data, as follows:

$$HD=ED\_data+[(2\times S\_data)+SF\_data+F\_data+NA\_data-DF\_data]\times 100/M\_serving. \quad (40)$$

For this group, the most healthful foods have an HD value less than or equal to 3.02, while less healthful foods have an HD value greater than 3.02 and less than or equal to 4.0, even less healthful foods have an HD value greater than 4.0 and less than or equal to 6.3 and the most unhealthful foods have an HD value greater than 6.3.

In certain embodiments, methods are provided for selecting and ingesting foods in a way that enables the consumer to control body weight, while simplifying the task of evaluating the relative healthfulness of a candidate food serving. With reference to FIG. 10, at the beginning of a selected period, such as a day or a week, a variable SUM is set 20 to 0. A consumer considers ingesting a candidate food serving and obtains 24 data representing its identity and/or its nutrient content and a predetermined group including the candidate food serving. In order to evaluate the desirability of ingesting the candidate food serving, the consumer obtains 26 food energy data and relative healthfulness data for the candidate food serving based on at least one of the data representing its (1) identity and (2) its nutrient content and group classification. Such food energy data and relative healthfulness is determined as disclosed hereinabove. In certain advantageous embodiments, such relative healthfulness is represented by distinctly different and suggestive colors and/or shapes on packaging or labeling of a food product, for example: a green star to represent those foods that provided the greatest satiety for minimal kcal as well as a nutritional profile which most closely complements public health guidelines; a blue triangle to represent foods with a nutritional profile that is not as closely aligned with public health recommendations but does have satiety and nutritional virtues; a pink square to represent foods that provide minimal satiety or nutritional value to overall intake but are likely to enhance the tastefulness or convenience of eating; and a white circle to represent foods that, while not making much of a contribution to overall nutrition or feelings of satiety, provide pleasure and can be part of a healthy eating plan when consumed in moderation.

Based on the food energy data and relative healthfulness data thus obtained, the consumer determines whether to accept or reject 30 the candidate food serving for consumption. For example, the consumer may wish to consume a snack food and must decide between a bag of fried corn chips and a bag of popcorn. He or she obtains their relative healthfulness data using one of the processes disclosed hereinabove, and decides 30 to select the popcorn because its healthfulness relative to the fried corn chips is more favorable than that of the fried corn chips. Thus, if the consumer decides 30 to reject a candidate food serving, the process returns to 24 to be repeated when the consumer again considers a candidate food serving for ingestion.

If the consumer has decided that a candidate food serving is sufficiently healthful or selected it in preference to another such candidate food serving, based on the obtained food energy data the consumer decides 30 whether to ingest the candidate food serving or to reject it. If the value of SUM would exceed predetermined maximum data if the consumer ingests the candidate food serving, the consumer decides 30 to reject it and the process returns to 24 to be repeated when the consumer again considers a candidate food serving for ingestion. If the consumer decides to ingest the candidate food serving, the food energy data is added 32 to SUM, the consumer ingests 36 the candidate food serving and the process returns to 24 to be repeated when the consumer again considers a candidate food serving for ingestion. It will be appreciated that steps 32 and 36 need not be carried out in the order illustrated. It will also be appreciated that the order in which the consumer considers the healthfulness data and the food energy data can vary depending on personal preference.

Where the consumer considers two candidate food servings, and accepts one to be ingested and rejects the other, in effect the process as illustrated in FIG. 10 is carried out twice, once for the candidate food serving accepted by the consumer and again for the rejected candidate food serving.

Figure 11:
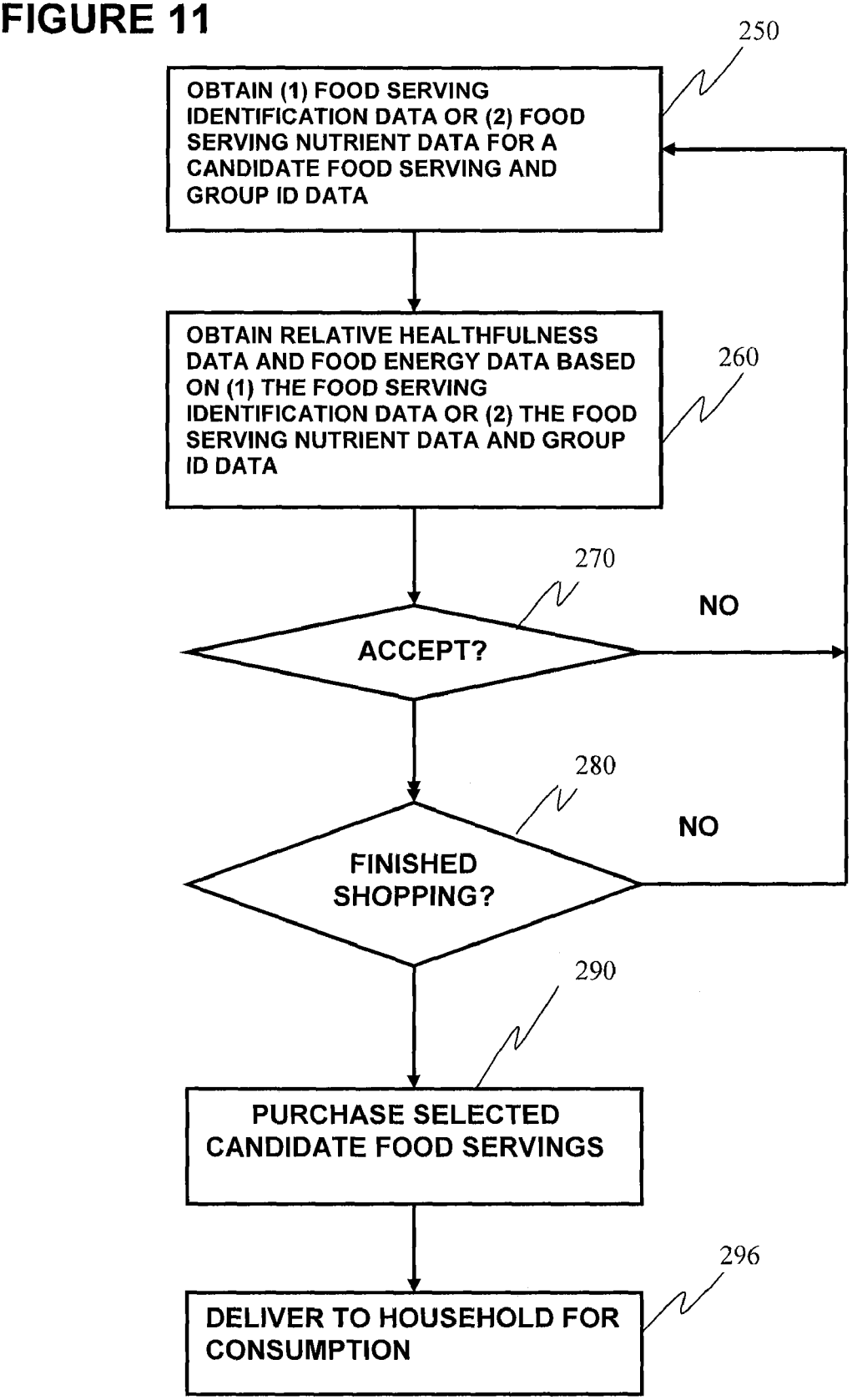
FIG. 11 is a flow chart illustrating certain disclosed processes for selecting and purchasing foods based on their food energy data and relative healthfulness data.

A method of selecting and purchasing food for consumption utilizing the relative healthfulness data and food energy data is illustrated in FIG. 11. When a consumer considers whether to purchase a given food offered for sale, the consumer supplies 250 data representing its identity and/or its nutrient content and a predetermined group including the food offered for sale. In order to evaluate the desirability of purchasing the food, the consumer obtains 260 relative healthfulness data and food energy data for the food based on at least one of the data representing its (1) identity and (2) its nutrient content and group classification. The food may be a packaged food, such as a Weight Watchers® packaged food that displays an image on its packaging representing the relative healthfulness data and food energy data of the product offered for sale. Instead it may be a packaged food that does not display such an image, so that the consumer inputs an identification of the packaged food, or else its classification in a respective predetermined food group and nutrient content, in a device such as a PDA or cellular telephone to obtain a display of the relative healthfulness data, as disclose more fully hereinbelow. It might also be a food such as produce that is unpackaged and the consumer may obtain the relative healthfulness data and food energy data in the same manner as for the packaged food lacking the image representing same.

Based on the relative healthfulness data and the food energy data, the consumer determines whether to accept or reject 270 the food for purchase. For example, the consumer may wish to purchase cookies and wishes to decide between two competing brands of the same kind of cookie. The relative healthfulness data and food energy data provide a simple and straightforward means of making this decision.

When the consumer has selected all of the foods to be purchased 280, he or she then purchases the selected foods 290 and delivers or has them delivered 296 to his/her household for consumption.

Figure 12:
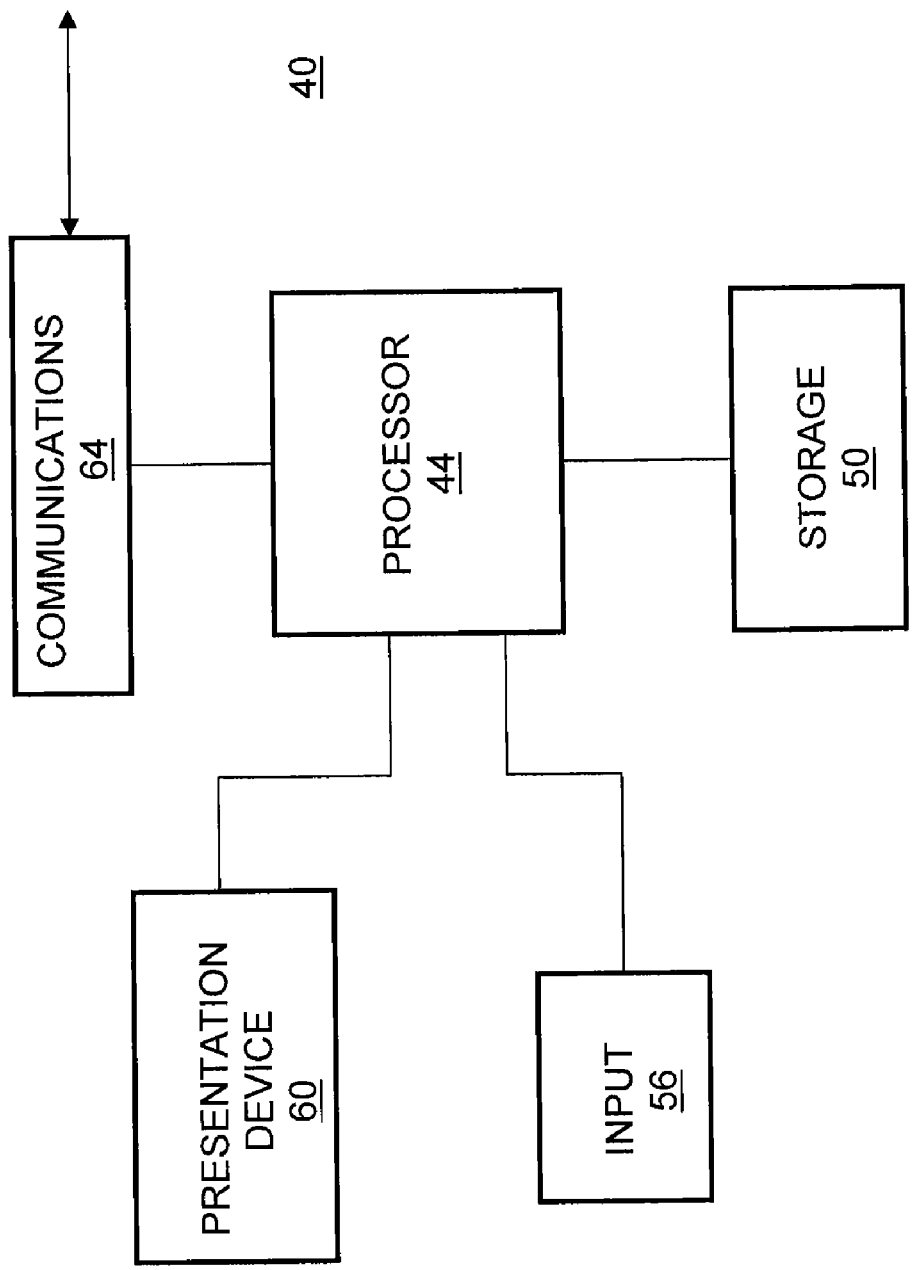
FIG. 12 illustrates certain embodiments of a data processing system useful in the processes disclosed herein.

FIG. 12 illustrates a data processing system 40 of certain embodiments useful in carrying out the processes of FIGS. 10 and 11. The data processing system 40 comprises a processor 44, a storage 50 coupled with the processor 44, an input 56 coupled with processor 44, a presentation device 60 coupled with processor 44 and communications 64 coupled with processor 44.

Where system 40 is implemented as a PDA, laptop computer, desktop computer or cellular telephone, in certain ones of such embodiments the input 56 comprises one or more of a keypad, a keyboard, a point-and-click device (such as a mouse), a touchscreen, a microphone, switch(es), a removable storage or the like, and presentation device 60 comprises an LCD display, a plasma display, a CRT display, a printer, lights, LED's or the like.

In certain ones of such embodiments, storage 50 stores data identifying the predetermined food groups and instructions for carrying out the processes necessary to produce the relative healthfulness data as summarized in equations (20) through (40) hereinabove. To obtain the relative healthfulness data, using input 56, the consumer inputs data identifying the food to be consumed or food offered for sale or an identification of its predetermined food group, and processor 44 retrieves appropriate instructions from storage 50 for carrying out the respective process for the identified food group. Storage 50 stores data associating food identity data with the corresponding food groups, so that when the consumer inputs food identification data, processor 44 accesses such data to identify its food group and then retrieves the appropriate processing instructions based thereon. Processor 44 then prompts the consumer, via presentation device 60, to enter the relevant ones of F_data, SF_data, DF_data, S_data, NA_data, M_serving, kcal DV, DD, and ED_data for a food to be purchased or candidate food serving depending on the process to be carried out. Processor 44 then processes the input data according to one of equations (20) through (40) to produce the relative healthfulness data. Processor 44 then controls presentation device 60 to display the relative healthfulness data to the consumer.

In certain ones of such embodiments, storage 50 stores the necessary weighting data and conversion factor data necessary to carry out one or more of the processes summarized in equations (1) through (15) hereinabove to produce food energy data. Using input 56, the consumer inputs the data PRO, CHO and FAT, the data PROm, CHOm and FATm, or the data PROm, Total_CHOm, DFm, Total_FATm, Sat_FATm, and ETOHm (as available), for a food or candidate food serving depending on the process to be carried out. Processor 44 retrieves the necessary weighting data and conversion factor data, as need be, from storage 50 and processes the input data according to one of equations (1) through (15) to produce the food energy data. Processor 44 then controls presentation device 60 to display the food energy data to the consumer.

In certain ones of such embodiments, storage 50 stores relative healthfulness data for a plurality of predetermined foods, which can be retrieved using an address based on an identification of the food input by the consumer using input 56. Processor 44 produces an address for the corresponding relative healthfulness data in storage 50 and reads the relative healthfulness data therefrom using the address. Processor 44 then controls presentation device 60 to display the relative healthfulness data to the consumer.

In certain ones of such embodiments, storage 50 stores food energy data for a plurality of predetermined foods, which can be retrieved using an address based on an identification of the food input by the consumer using input 56. Processor 44 produces an address for the corresponding food energy data in storage 50 and reads the food energy data therefrom using the address. Processor 44 then controls presentation device 60 to display the food energy data to the consumer.

Figure 13:
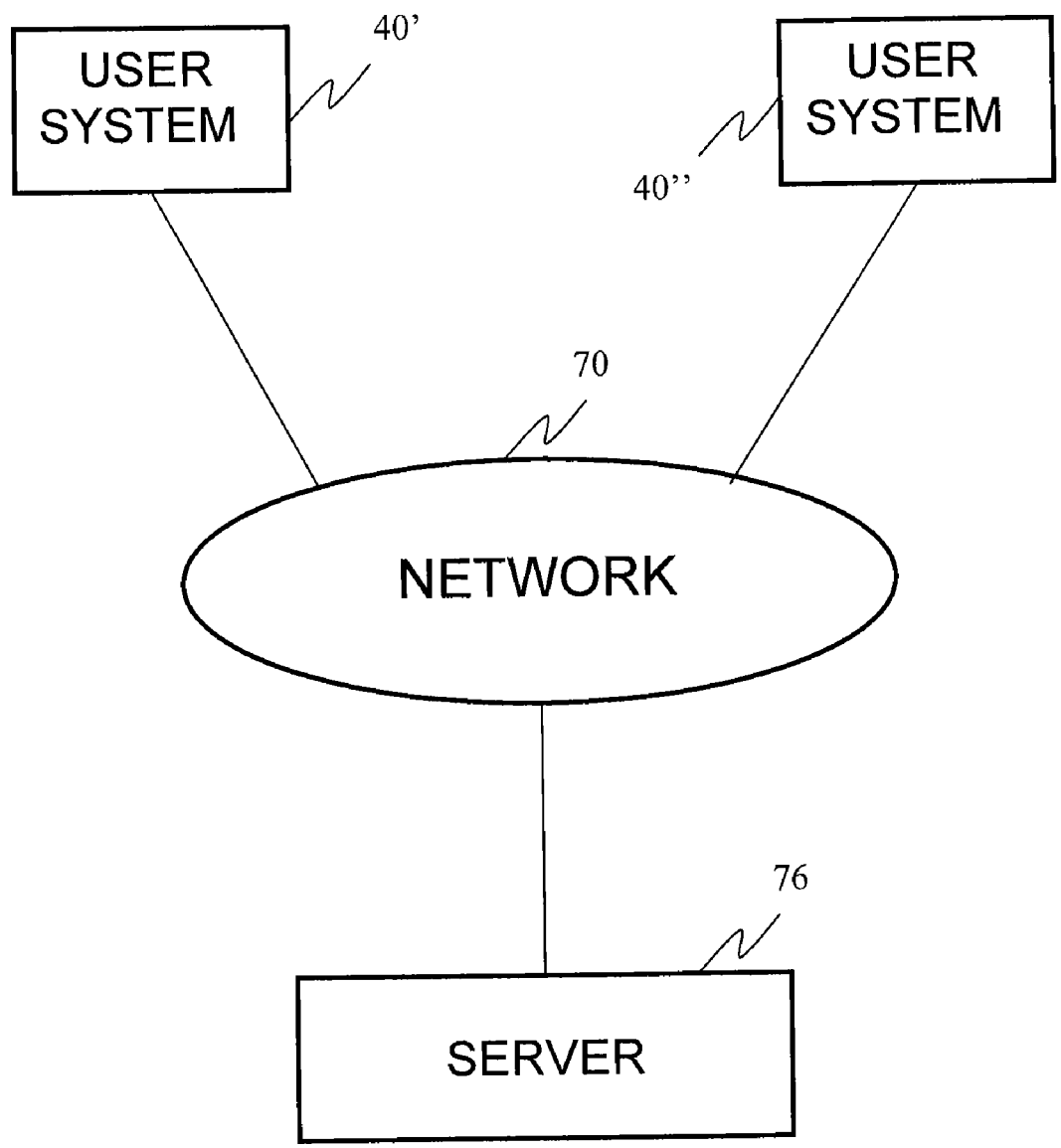
FIG. 13 illustrates a client/server system useful in the processes disclosed herein.

In certain ones of such embodiments, the relative healthfulness data and/or the food energy data stored in storage 50 is downloaded from a server via a network. With reference to FIG. 13, in certain embodiments a plurality of data processing systems 40' and 40", each corresponding to data processing system 40 access a server 76 via a network 70 to obtain the relative healthfulness data and/or the food energy data, either to obtain a database of such data or to update such a database stored in their storage 50. Network 70 may be a LAN, WAN, metropolitan area network or an internetwork, such as the Internet. Server 76 stores relative healthfulness data and/or food energy data for a large number and variety of foods and candidate food servings which have been produced thereby, obtained from another host on network 70 or a different network, or input from a removable storage device or via an input of server 76.

In certain ones of such embodiments, processor 44 of one of data processing systems 40' and 40" receives the input data from input 56 and the consumer, and controls communications 64 to communicate such data to server 76 via network 70. Server 76 either retrieves the corresponding relative healthfulness data and/or the food energy data from a storage thereof (not shown for purposes of simplicity and clarity), or produces the relative healthfulness data from the received data using the process identified by the food group identification data and/or the food energy data, as appropriate, and communicates the produced data to communications 64. Processor 44 then controls presentation device 60 to display the received data to the consumer.

The systems of FIGS. 12 and 13 are configured in certain embodiments to produce meal plan data for a person on request. A meal plan for a given person is based on a personal profile of the person and relative healthfulness data and food energy data produced for a variety of foods, either prior to the request for the meal plan data or upon such request. The personal profile includes such data as may be necessary to retrieve or produce a meal plan tailored to the needs and/or desires of the requesting person, and can include data such as the person's weight, height, body fat, gender, age, attitude, physical activity level, weight goals, race, religion, ethnicity, health restrictions and needs, such as diseases and injuries, and consequent dietary restrictions and needs. This data is entered by the requesting person via input 56 of the system 40 in FIG. 12, and stored as a personal profile either by processor 44 in storage 50, or communicated by communications 64 to be stored by server 76.

In certain embodiments, processor 44 accesses appropriate instructions from storage 50 to produce a plurality of meal plans each designed to fulfill predetermined criteria, such as a low-fat diet, a low carbohydrate diet, an ethnically or religiously appropriate diet, or the like. Criteria and methods for producing such diets are well known and encompass the criteria and methods disclosed by US published patent application No. 2004/0171925, published Sep. 2, 2004 in the names of David Kirchoff, et al. and assigned to the assignee of the present application. US 2004/0171925 is hereby incorporated by reference herein in its entirety.

Processor 44 also obtains healthfulness data and food energy data produced as described hereinabove for the various foods in or to be included in the meal plan data, and selects and/or substitutes foods for the meal plan based on the healthfulness data and the food energy data. In certain ones of such embodiments, for a person attempting to lose body weight processor 44 selects and/or substitutes the foods based on the food energy data in order to ensure that the person can achieve the desired weight loss safely. In certain ones of such embodiments, processor 44 selects and/or substitutes the foods in order to maximize the healthfulness of the foods in the meal plan data overall based on their relative healthfulness data. In certain ones of such embodiments, processor 44 selects and/or substitutes the foods in order to achieve a minimum target level of healthfulness of the foods in the meal plan data based on their relative healthfulness data. In certain ones of such embodiments, the processor 44 produces meal plan data matched to predetermined criteria and stores the data in storage 50 for subsequent access upon a request for meal plan data. Upon receipt of such a request, processor 44 accesses the meal plan data based on a requesters profile data presents it to the requester via presentation device 60.

Once the meal plan data is been thus produced, processor 44 controls presentation device 60 to present the meal plan data to the requesting person. In certain embodiments in which the server 76 obtains the meal plan data, server 76 communicates the meal plan data to communications 64 for presentation to the requesting person via presentation device 60. In certain ones of such embodiments, the server 76 produces meal plan data matched to predetermined criteria and stores the data for subsequent access upon a request for meal plan data. Upon receipt of such a request from one of systems 40' and 40", server 76 accesses the meal plan data based on a requester's profile data and communicates it to the requesting system for presentation to the requester.

Consumers often are confused by the extensive nutritional information printed on the packaging of foods. Some simply find it too burdensome to read such information, often in relatively fine print so that it can all fit in the available space, and then weigh the relative merits and undesirable aspects of such information. While the Traffic Light system provides a degree of simplification to this process, it is still necessary for the consumer to look for additional information on the packaging in order to acquire information desired by those attempting to maintain, lose or gain weight.

Figure 14:
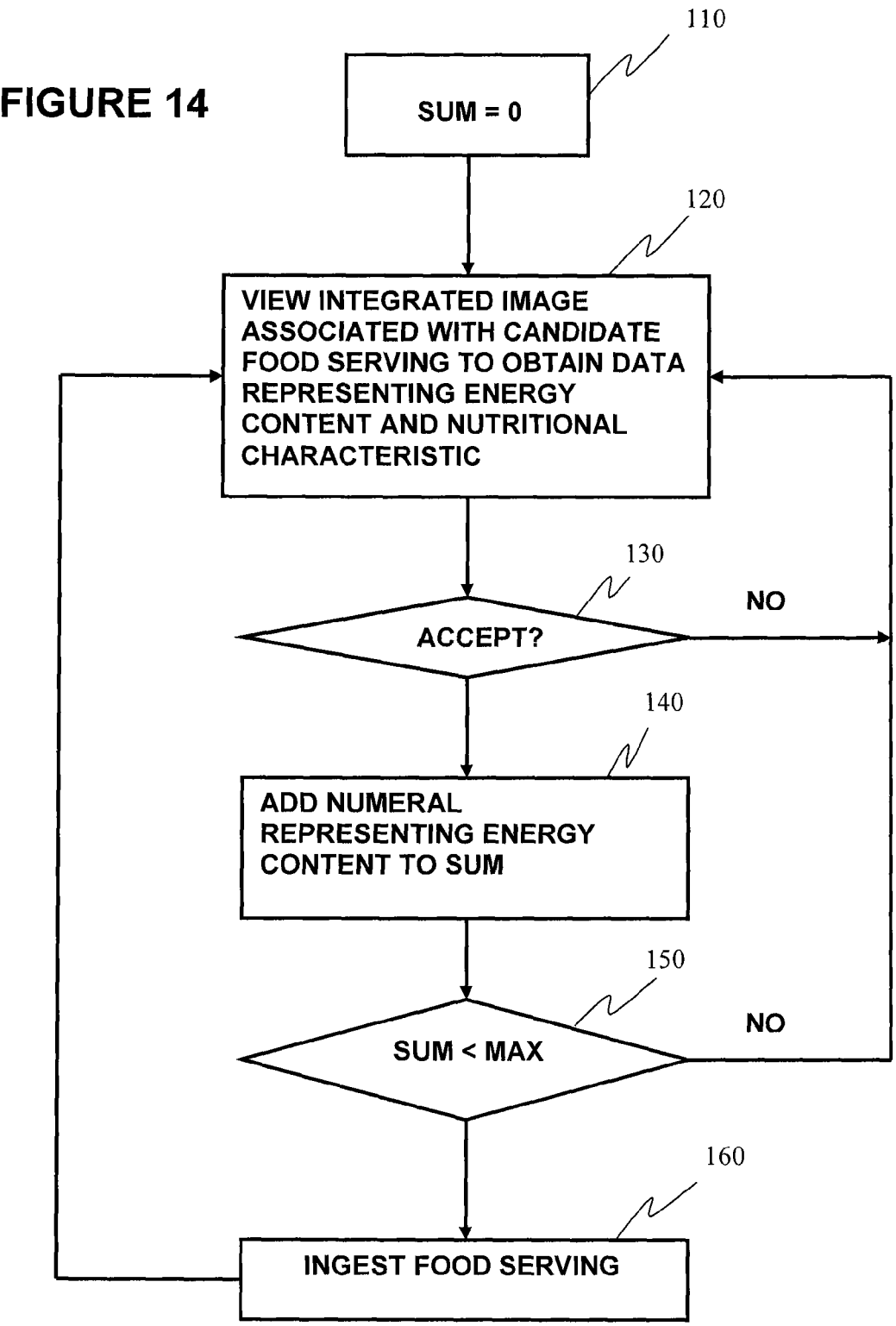
FIG. 14 is a flow chart illustrating certain disclosed processes for weight control and selecting foods to be consumed based on data representing their energy content and a desired nutritional characteristic.

In certain embodiments, methods are provided for selecting and ingesting foods in a way that enables the consumer to control body weight, while simplifying the task of evaluating the desirability of each of various foods based on multiple criteria. With reference to FIG. 14, at the beginning of a predetermined period, such as a day or a week, the consumer or a data processing system sets 110 a variable "SUM" equal to zero.

When the consumer considers whether to ingest a candidate food serving, the consumer views 120 an integrated image including both a numeral representing an energy value of the food serving and an auxiliary image feature representing a further nutritional quality of the food serving. In certain ones of such embodiments, the further nutritional quality comprises the relative healthfulness of the candidate food serving. Such relative healthfulness may be determined as disclosed in this application, or in another manner. In certain advantageous embodiments, such relative healthfulness is represented by distinctly different and suggestive image colors, shades, shapes, brightness, or textures. In certain ones of such embodiments, the further nutritional quality represents a relative heart healthiness of the candidate food serving, while in others it represents sugar content for use by diabetic consumers. In certain ones of such embodiments, the further nutritional quality represents an amount, presence or absence of a particular nutrient or nutrients. For example, body builders may wish to know the amount of protein in a serving of a particular candidate food serving or whether such protein includes all essential amino acids.

The integrated image may be imprinted on the packaging or label of the candidate food serving, or it may be displayed by a data processing system, such as a PDA, cellular telephone, laptop computer or desktop computer, as described more fully hereinbelow. It may also be displayed in a printed document.

Figure 15A:
FIGS. 15A through 15D illustrate exemplary images for use in conveying energy content data and nutritional characteristic data of foods.

The integrated image in certain embodiments comprises a numeral representing the energy content of an associated food displayed on a background colored to represent a further nutritional quality of the candidate food serving. An example of such an integrated image is provided in FIG. 15A wherein the numeral comprises an integer on a green background with a triangular border. In certain advantageous embodiments the color green is used to represent a favorable nutritional quality relative to other candidate food servings in a predetermined food group including the associated candidate food serving. For example, green may represent those foods that provided the greatest satiety for minimal energy content as well as a nutritional profile which most closely complements public health guidelines. The color blue may be used to represent foods having a relatively lower healthfulness profile, such as foods with a nutritional profile that is not as closely aligned with public health recommendations but does have satiety and nutritional virtues. The color pink may be used to represent foods with a relatively lower healthfulness profile than those coded blue, such as foods that provide minimal satiety or nutritional value to overall intake but are likely to enhance the tastefulness or convenience of eating. The color white may be used to represent foods falling within the lowest healthfulness profile, such as foods that, while not making much of a contribution to overall nutrition or feelings of satiety, provide pleasure and can be part of a healthy eating plan when consumed in moderation.

Figure 15B:
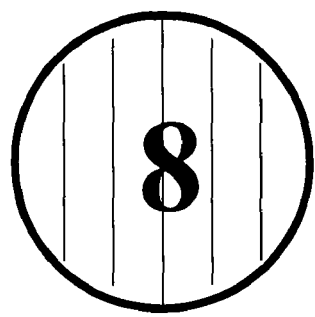

A further example of such an integrated image is provided in FIG. 15B wherein the numeral comprises a different integer within a circular border. The shape of the border may be used by itself to represent relative healthfulness or another nutritional characteristic, while the numeral represents food energy data. In other embodiments, both the shape of the border and a color, shading or texture enclosed by the border can provide the data for the nutritional characteristic represented by the shape in FIG. 15B.

Figure 15C:

Still another example of an integrated image is provided in FIG. 15C wherein the numeral 6.5 appears within the image to provide food energy data, and the rectangular border of the image, with or without a color, shading or texture code, to provide the data for the further nutritional characteristic.

Figure 15D:
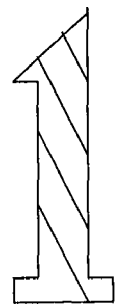

FIG. 15D illustrates a still further integrated image in which a numeral representing an energy content of a candidate food serving is colored to represent the further nutritional characteristic of the candidate food serving. While the numeral of FIG. 15D is not enclosed within a border, in certain embodiments a border is provided. In still other embodiments, the numeral is shaded or textured to provide the data for the further nutritional characteristic. Various other shapes may also be used, such as a star, oval or donut shape. Any shapes, colors, textures and shadings may be used, whether alone or in combination to provide the data for the additional nutritional characteristic. Moreover, arabic numerals need not be used, so that any data representing numerical data (such as roman numerals) can serve as the numeral data to represent energy content.

With reference again to FIG. 14, based on the data provided by the integrated image, that is, the energy content data and the further nutritional quality data provided thereby, the consumer determines whether to accept or reject 130 the candidate food serving for consumption. For example, the consumer may wish to consume a snack food and must decide between a bag of fried corn chips and a bag of popcorn. He or she views the integrated image on each bag, and decides to consume the popcorn both because its energy content and healthfulness relative to the fried corn chips as revealed by the integrated image are more favorable than those of the fried corn chips. The integrated image thus provides an easily viewed and readily understood evaluation of multiple nutritional qualities of a candidate food serving.

In certain embodiments, with or without the use of a data processing system, the consumer adds the data represented by the numeral in the integrated image associated with the candidate food serving to the SUM 140, and if the SUM is less than a predetermined daily or weekly maximum MAX 150, the consumer ingests 160 the candidate food serving. In the alternative, the consumer first ingests the candidate food serving and then adds the number data represented by the numeral in the integrated image to SUM. For example, the consumer might not know the precise value of SUM plus the number data, but is aware that it is relatively low compared to MAX.

Figure 16:
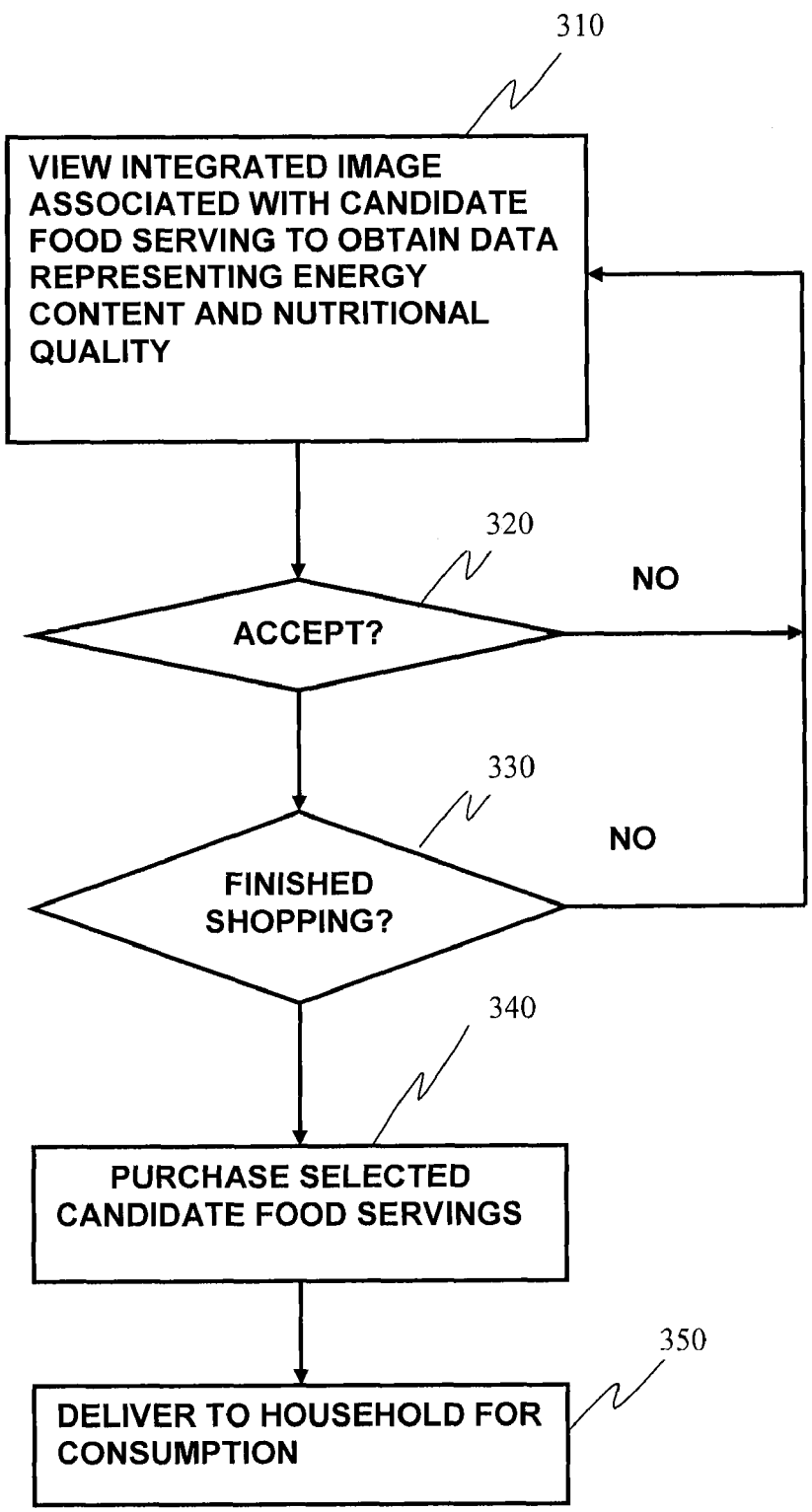
FIG. 16 is a flow chart illustrating a process for selecting and purchasing foods based on their energy content and a desired nutritional characteristic.

A method of selecting and purchasing food for consumption utilizing the integrated image is illustrated in FIG. 16. When a consumer considers whether to purchase a given food for consumption, the consumer views 310 an integrated image associated with the food including both a numeral representing an energy value of the food and an auxiliary image feature representing a further nutritional quality of the food. The food may be a packaged food, such as a Weight Watchers® packaged food that displays the integrated image on its packaging. Instead it may be a packaged food that does not display such an image, so that the consumer inputs an identification of the packaged food in a device such as a PDA or cellular telephone to obtain a display of the integrated image for evaluation, as disclose more fully hereinbelow. It might also be a food such as produce that is unpackaged and the consumer may obtain an associated integrated image in the same manner as for the packaged food lacking the image.

Based on the data provided by the integrated image, that is, the energy content data and the further nutritional quality data provided thereby, the consumer determines whether to accept or reject 320 the food for purchase. For example, the consumer may wish to purchase cookies and wishes to decide between two competing brands of the same kind of cookie. Each may have the same energy content, so that the consumer may wish to choose the brand having a more favorable healthfulness based on differing colors, shapes, textures, shadings or combinations thereof seen in the integrated image on each package. Or else if each has an image having the same auxiliary image feature, the consumer may wish to select the brand having a lower energy content per serving.

When the consumer has selected all of the foods to be purchased 330, he or she then purchases the selected foods 340 and delivers or has them delivered 350 to his/her household for consumption.

With reference again to FIG. 12 the data processing system 40 illustrated therein is useful in certain embodiments for carrying out the processes of FIGS. 14 and 16. In certain ones of such embodiments, storage 50 stores (A) the weighting data and conversion factors necessary to carry out one or more of the processes summarized in equations (1) through (15) hereinabove to produce food energy data, and (B) data identifying the predetermined food groups and instructions for carrying out the processes necessary to produce the relative healthfulness data as summarized in equations (20) through (40) hereinabove.

For producing relative healthfulness data for the food to be consumed or the food offered for sale, using input 56, the consumer inputs data identifying the food to be consumed or food offered for sale or an identification of its predetermined food group, and processor 44 retrieves appropriate instructions from storage 50 for carrying out the respective process for the identified food group. Storage 50 stores data associating food identity data with the corresponding food groups, so that when the consumer inputs food identification data, processor 44 accesses such data to identify its food group and then retrieves the appropriate processing instructions based thereon. Processor 44 then prompts the consumer, via presentation device 60, to enter the relevant ones of F_data, SF_data, DF_data, S_data, NA_data, M_serving, kcal DV, DD and ED_data for a food to be purchased or candidate food serving depending on the process to be carried out. Processor 44 then processes the input data according to one of equations (20) through (40) to produce the relative healthfulness data.

For producing food energy data for the food to be consumed or the food offered for sale, using input 56, the consumer inputs appropriate data (as disclosed hereinabove), for a food or candidate food serving depending on the process to be carried out. Processor 44 retrieves the necessary weighting data and conversion factors, as need be, from storage 50 and processes the input data according to one of equations (1) through (15) to produce the food energy data.

Using the relative healthfulness data and food energy data thus produced, processor 44 uses this data to retrieve an image dataset from storage 50 including data for producing the auxiliary image feature corresponding to the healthfulness data and numeral data corresponding to the food energy data, and controls presentation device 60 to display an integrated image based on the image dataset depicting the numeral and the auxiliary image feature to convey the energy content and the relative healthfulness of the food offered for sale or to be consumed to the consumer.

In certain ones of such embodiments, storage 50 stores relative healthfulness data and food energy data for a plurality of predetermined foods, which can be retrieved using an address based on an identification of the food input by the consumer using input 56. Processor 44 produces addresses for the corresponding relative healthfulness data and food energy data in storage 50 and reads the relative healthfulness data and food energy data therefrom using the addresses. Using the relative healthfulness data and food energy data thus produced, processor 44 uses this data to retrieve an image dataset from storage 50 including data for producing the auxiliary image feature corresponding to the healthfulness data and numeral data corresponding to the food energy data, and controls presentation device 60 to display the integrated image.

In certain ones of such embodiments, storage 50 stores the image datasets for the integrated images for a plurality of predetermined foods, which can be retrieved using an address based on an identification of the food input by the consumer using input 56. Based on the food identification data input by the consumer using input 56, processor 44 produces an address corresponding to the input data and retrieves an image dataset from storage 50 corresponding thereto to controls presentation device 60 to display the integrated image for the food thus identified.

In certain ones of such embodiments, the relative healthfulness data and food energy data stored in storage 50 is downloaded from a server via a network. With reference again to FIG. 13, a plurality of data processing systems 40' and 40", each corresponding to data processing system 40 access a server 76 via a network 70 to obtain the relative healthfulness data and food energy data, either to obtain a database of relative healthfulness data and food energy data or to update such a database stored in their storage 50. Network 70 may be a LAN, WAN, metropolitan area network or an internetwork, such as the Internet. Server 76 stores relative healthfulness data and food energy data for a large number and variety of foods and candidate food servings which have been produced thereby, obtained from another host on network 70 or a different network, or input from a removable storage device or via an input of server 76.

In certain ones of such embodiments, processor 44 of one of data processing systems 40' and 40" receives the input data from input 56 and the consumer, and controls communications 64 to communicate such data to server 76 via network 70. Server 76 either retrieves the corresponding relative healthfulness data and food energy data from a storage thereof (not shown for purposes of simplicity and clarity), or produces the relative healthfulness data and food energy data from the received data using the process identified by the food group identification data and a selected one of the food energy data production processes, as appropriate, and communicates the relative healthfulness data and food energy data to communications 64. Processor 44 then retrieves the corresponding image dataset from storage 50 and controls presentation device 60 to display the corresponding integrated image to the consumer.

In certain ones of such embodiments, processor 44 of one of data processing systems 40' and 40" receives the input data from input 56 and the consumer, and controls communications 64 to communicate such data to server 76 via network 70. Server 76 retrieves a corresponding image dataset for the corresponding integrated image and communicates it to communications 64. Processor 44 then uses the received image dataset to control the presentation device 60 to display the integrated image to the consumer.

Figure 17:
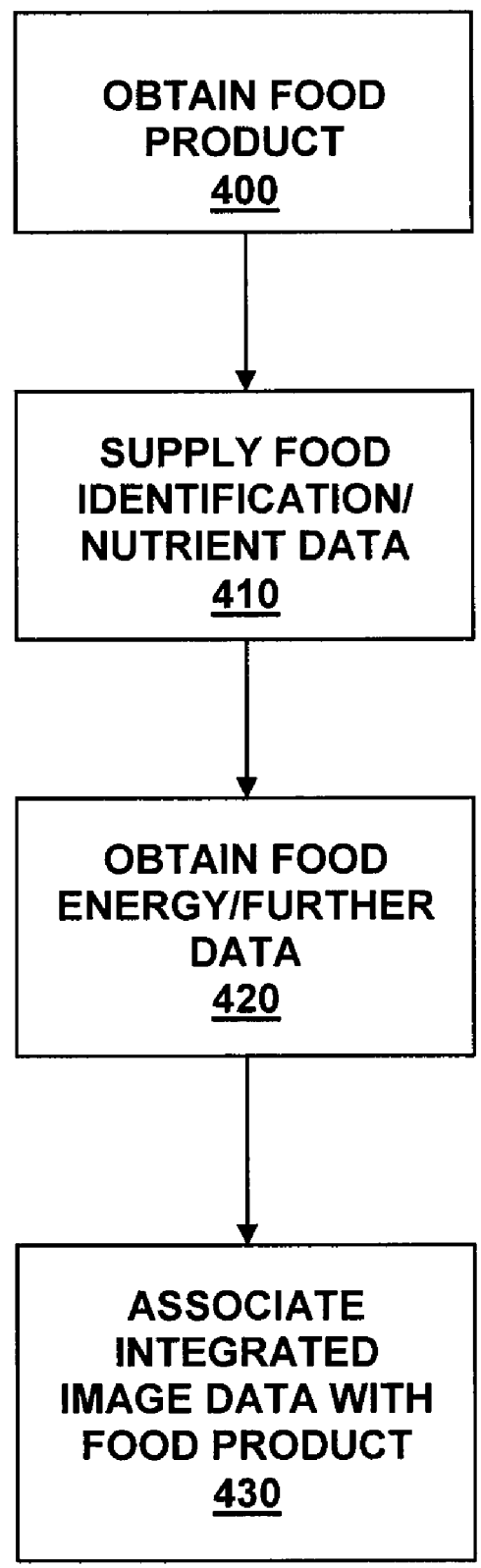
FIG. 17 is a flow chart used to illustrate certain embodiments of a process for producing a food product having an integrated image associated therewith.

FIG. 17 is a flow chart used to illustrate certain embodiments of a process for producing a food product having the integrated image associated therewith. A food product is obtained 400, whether by producing the food product, by retrieving it from inventory or receiving a delivery thereof. Accordingly, the food product may be a processed food product, or it may be a raw food product, such as an agricultural product or seafood.

At least one of food identification data and food nutrient data of the food product is supplied 410. The food identification data may be the name of the food, a stock keeping unit or other data as described hereinbelow. In certain ones of such embodiments, food energy data for the food product and further data representing a further nutritional characteristic of the food product, such as relative healthfulness data, is obtained 420 based on the food identification data or the food nutrient data, using one of the processes disclosed hereinabove.

In certain ones of such embodiments, the food identification data is input to a data processing system storing food energy data and such further data for one or more food products. In this example, the food identification data may be a name of the food product, an identifier such as a stock keeping unit, or data which associates the food product with its respective stored food energy data. In certain ones of such embodiments, such food nutrient data is supplied to a data processing system as may be required to produce food energy data and the further data for the food product using one of the processes disclosed hereinabove. In certain ones of such embodiments, the data is obtained from an appropriate record or calculated in accordance with one of the processes disclosed hereinabove.

Using the food energy data and the further data, a processor of the data processing system retrieves an image dataset from a storage of the data processing system including data for producing the auxiliary image feature corresponding to the further nutritional characteristic of the food product, such as its relative healthfulness, and numerical data corresponding to the food energy data, so that the integrated image may be produced.

In certain ones of such embodiments, a storage of the data processing system stores image datasets corresponding to food identification data and/or food nutrient data. The at least one of food identification data and food nutrient data of the food product is used by a processor of the data processing system to retrieve the image dataset from a storage of the data processing system.

In certain ones of such embodiments, the integrated image data is obtained for a known food product, with or without the use of a data processing system. For example, the integrated image data may be obtained from publicly available packaging or labels, as data obtained in electronic form via a network, such as the Internet or as data obtained from other printed or electronically accessible sources.

The integrated image data obtained as disclosed hereinabove is associated 430 with the food product. In certain ones of such embodiments, the integrated image data is printed, applied or otherwise made visible on packaging of the food product. In certain ones of such embodiments, the integrated image data is made visible on a label affixed on or to the food product, such as an adhesive-backed label on produce or a label tethered to a food product.

In certain embodiments, the food energy data and the relative healthfulness data are associated with the food product in a form other than the integrated image, such as separately displayed data.

The foregoing disclosure of certain embodiments provides exemplary ways of implementing the principles of the present invention, and the scope of the invention is not limited by this disclosure. This invention can be embodied in many different forms and should not be construed as limited to the embodiments set forth herein; rather, these embodiments are provided so that this disclosure will be thorough and complete to those skilled in the art. The scope of the present invention is instead defined by the following claims.

What is claimed is:

1. A process for controlling body weight in a human being, comprising:
    a) obtaining weight of protein, PRO(m), for each candidate food servings;
    b) obtaining weight of fat, FAT(m), for each candidate food serving;
    c) obtaining weight of non-dietary fiber carbohydrates, CHO(m), for each candidate food serving;
    d) obtaining weight of dietary fiber, DF(m), for each candidate food serving;
    e) inputting the obtained weights of each candidate food serving in a data processing system;
    f) determining a whole number value for each candidate food serving via a processor of the data processing system, comprising:
        1) determining, via the processor, food energy data for each candidate food serving, FED value, based at least in part on three of:
            i) W(PRO)×Cp×PRO(m), wherein W(PRO) is a metabolic efficiency factor of protein and wherein Cp is a energy conversion factor of protein,
            ii) W(FAT)×Cf×FAT(m), wherein W(FAT) is a metabolic efficiency factor of fat and wherein Cf is a energy conversion factor of fat,
            iii) W(CHO)×Cc×CHO(m), wherein W(CHO) is a metabolic efficiency factor of carbohydrate and wherein Cc is a energy conversion factor of carbohydrate, and
            iv) W(DF)×Cdf×DF(m), wherein W(DF) is a metabolic efficiency factor of dietary fiber and wherein Cdf is a energy conversion factor of dietary fiber;
        2) dividing the determined FED value by a factor data obtained from a storage device and saving the result as whole number value for each candidate food serving;
    g) determining a daily whole number benchmark data for the human being, wherein the daily whole number benchmark data for the human being is determined based on daily total energy expenditure of the human being;
    h) during a day, selecting food servings from the candidate food servings, by determining via the data processing system, each candidate food serving's whole number value;
    i) automatically displaying, by the data processing system, a sum of whole number values of consumed food servings via a presentation device;
    j) consuming the selected food servings until the sum of whole number values of consumed food servings is less than or equal to the daily whole number benchmark data saved in said storage device; and
    k) repeating at least steps (a)-(j) in successive days to control body weight.

2. The process of claim 1, wherein W (PRO) is selected from a range 0.7<=W(PRO)<=0.9, W(CHO) is selected from a range 0.9<=W(CHO)<=0.99, W(FAT) is selected from a range 0.9<=W(FAT)<=1.0 and W(DF) is selected from a range 0<=W(DF)<=0.5.

3. The process of claim 1, wherein W (PRO) is selected from a range 0.75<=W(PRO)<=0.88, W(CHO) is selected from a range 0.92<=W(CHO)<=0.97, W (FAT) is selected from a range 0.95<=W(FAT)<=1.0 and W(DF) is selected from a range 0<=W(DF)<=0.25, wherein PRO(m), CHO(m), FAT(m) and DF(m) are expressed in grams, and wherein Cp is selected as 4 kilocalories/gram, Cc is selected as 4 kilocalories/gram, Cf is selected as 9 kilocalories/gram and Cdf is selected as 4 kilocalories/gram.

4. The process of claim 1, wherein the factor data is a whole number selected from a range between 20 and 100.

5. The process of claim 1, wherein each step of obtaining PRO(m), CHO(m), FAT(m) and DF(m) comprises electronically receiving, by the data processing system, each respective weight.

6. A data processing system for assisting a human being to control his or her body weight, comprising:
 a) a data gathering device, wherein the data gathering device is substantially designed to:
  i) obtain weight of protein, PRO(m) for each candidate food servings,
  ii) obtain weight of fat, FAT(m), for each candidate food serving,
  iii) obtain weight of non-dietary fiber carbohydrates, CHO(m), for each candidate food serving, and
  iv) obtain weight of dietary fiber, DF(m), for each candidate food serving;
 b) at least one computer module to determine a whole number value for each candidate food serving via a processor of the data processing system, comprising:
  1) computer instructions to determine, via the first processor, food energy data for each candidate food serving, FED value, based at least in part on three of:
   i) $W(PRO) \times Cp \times PRO(m)$, wherein $W(PRO)$ is a metabolic efficiency factor of protein and wherein $Cp$ is a energy conversion factor of protein,
   ii) $W(FAT) \times Cf \times FAT(m)$, wherein $W(FAT)$ is a metabolic efficiency factor of fat and wherein $Cf$ is a energy conversion factor of fat,
   iii) $W(CHO) \times Cc \times CHO(m)$, wherein $W(CHO)$ is a metabolic efficiency factor of carbohydrate and wherein $Cc$ is a energy conversion factor of carbohydrate, and
   iv) $W(DF) \times Cdf \times DF(m)$, wherein $W(DF)$ is a metabolic efficiency factor of dietary fiber and wherein $Cdf$ is a energy conversion factor of dietary fiber;
  2) computer code to divide the determined FED value by a factor data obtained from a storage device and saving the result as the whole number value for each candidate food serving;
 c) the at least one computer module to obtain a daily whole number benchmark data for the human being, wherein the daily whole number benchmark data is determined based on daily total energy expenditure of the human being;
 d) the at least one computer module to determine, via the data processing system, each candidate food serving's whole number value;
 e) the at least one computer module to automatically display, by the data processing system, a sum of whole number values of consumed food servings via a presentation device; and
 f) the at least one computer module to determine whether the sum of whole number values of consumed food servings, during a day, is less than or equal to the daily whole number benchmark data saved in said storage device.

7. The system of claim 6, wherein W (PRO) is selected from a range $0.7 <= W(PRO) <= 0.9$, W(CHO) is selected from a range $0.9 <= W(CHO) <= 0.99$, W(FAT) is selected from a range $0.9 <= W(FAT) <= 1.0$ and W(DF) is selected from a range $0 <= W(DF) <= 0.5$.

8. The system of claim 6, wherein W (PRO) is selected from a range $0.75 <= W(PRO) <= 0.88$, W(CHO) is selected from a range $0.92 <= W(CHO) <= 0.97$, W (FAT) is selected from a range $0.95 <= W(FAT) <= 1.0$ and W(DF) is selected from a range $0 <= W(DF) <= 0.25$, wherein PRO(m), CHO(m), FAT(m) and DF(m) are expressed in grams, and wherein Cp is selected as 4 kilocalories/gram, Cc is selected as 4 kilocalories/gram, Cf is selected as 9 kilocalories/gram and Cdf is selected as 4 kilocalories/gram.

9. The system of claim 6, wherein the factor data is a whole number selected from a range between 35 and 70.

10. The system of claim 6, wherein the data gathering device receives PRO(m), CHO(m), FAT(m) and DF(m).

11. A process for selecting a food product based on the food product's health effect on a human being, comprising:
 (a) obtaining data about nutrients of a first food product;
 (b) obtaining data about nutrients of a second food product;
 (c) inputting the obtained data of the first and the second food products in a data processing system;
 (d) associating, by a processor of the data processing system, the first and the second food products with a metagroup, wherein the metagroup is determined based at least, in part, on:
  i) a first similarity in nutrients among different food products, and
  ii) a second similarity in usage of different food products within context of a specific diet, and wherein the metagroup is associated with a specific healthfulness formula stored in a storage device of the data processing system, wherein the healthfulness formula is a linear combination of at least a plurality of the following data about nutrients of a food product: i) fat content, ii) sugar content, iii) sodium content, iv) energy, v) saturated fat, and vi) dietary fiber content;
 (e) calculating a first healthfulness data for the first food product based on the healthfulness formula of the metagroup via the processor of the data processing system;
 (f) calculating a second healthfulness data for the second food product based on the healthfulness formula of the metagroup via the processor of the data processing system;
 (g) comparing the first healthfulness data to the second healthfulness data via the processor of the data processing system; and
 (h) providing an outcome of the comparing step which is display on a presentation device of the data processing system.

12. The process of claim 11, wherein the first and the second food products are ranked based on each respective healthfulness data in to one of the following group:
 i) most healthful, ii) less healthful; iii) even less healthful, and iv) least healthful.

13. The process of claim 11, wherein the data about nutrients of a food product is determined, by the data processing system, based at least, in part, on a ratio of an amount of a specific nutrient in a food product to a recommended daily allowance amount for the specific nutrient based on the specific diet.

14. The process of claim 11, wherein the similarity in nutrients among different food products is determined, by the data processing system, based on whether content of a specific nutrient in a food product falls within a pre-determined range of values for the specific nutrient.

15. The process of claim 11, wherein the displayed outcome of the comparing step comprises unique identifier regarding the food product's health effects.

16. A data processing system for selecting a food product based on the food product's health effect on a human being, comprising:
 a) a data gathering device, wherein the data gathering device is substantially designed to:

(i) obtaining data about nutrients of a first food product, and
(ii) obtaining data about nutrients of a second food product;
b) at least one computer module for associating the first and the second food products with a metagroup, wherein the metagroup is determined based at least, in part, on:
  i) a first similarity in nutrients among different food products, and
  ii) a second similarity in usage of different food products within context of a specific diet, and wherein the metagroup is associated with a specific healthfulness formula stored in a storage device of the data processing system, wherein the healthfulness formula is a linear combination of at least a plurality of the following data about nutrients of a food product: i) fat content, ii) sugar content, iii) sodium content, iv) energy, v) saturated fat, and vi) dietary fiber content;
c) the at least one computer module for calculating a first healthfulness data for the first food product based on the healthfulness formula of the metagroup via the processor of the data processing system;
d) the at least one computer module for calculating a second healthfulness data for the second food product based on the healthfulness formula of the metagroup via the processor of the data processing system;
e) the at least one computer module for comparing the first healthfulness data to the second healthfulness data via the processor of the data processing system; and
f) the at least one computer module for providing an outcome of the comparing step which is display on a presentation device of the data processing system.

17. The system of claim 16, wherein the first and the second food products are ranked, by the data processing system, based on each respective healthfulness data in to one of the following group: i) most healthful, ii) less healthful; iii) even less healthful, and iv) least healthful.

18. The system of claim 16, wherein the data about nutrients of a food product is determined, by the data processing system, based at least, in part, on a ratio of an amount of a specific nutrient in a food product to a recommended daily allowance amount for the specific nutrient based on the specific diet.

19. The system of claim 16, wherein the similarity in nutrients among different food products is determined, by the data processing system, based on whether content of a specific nutrient in a food product falls within a pre-determined range of values for the specific nutrient.

20. The process of claim 16, wherein the displayed outcome of the comparing step comprises unique identifier regarding the food product's health effects.

21. A process for controlling body weight in a human being, comprising:
(a) obtaining data about nutrients of a first food product;
(b) obtaining data about nutrients of a second food product;
(c) wherein the steps of obtaining the data about nutrients of a food product, comprise:
  i) obtaining weight of protein, PRO(m), for each candidate food servings;
  ii) obtaining weight of fat, FAT(m), for each candidate food serving;
  iii) obtaining weight of non-dietary fiber carbohydrates, CHO(m), for each candidate food serving;
  iv) obtaining weight of dietary fiber, DF(m), for each candidate food serving;
(d) inputting the obtained data of the first and the second food products in a data processing system;
e) determining a whole number value for each food product via a processor of the data processing system, comprising:
  1) determining, via the processor, food energy data for each food product, FED value, based at least in part on three of:
    i) $W(PRO) \times Cp \times PRO(m)$, wherein $W(PRO)$ is a metabolic efficiency factor of protein and wherein $Cp$ is a energy conversion factor of protein,
    ii) $W(FAT) \times Cf \times FAT(m)$, wherein $W(FAT)$ is a metabolic efficiency factor of fat and wherein $Cf$ is a energy conversion factor of fat,
    iii) $W(CHO) \times Cc \times CHO(m)$, wherein $W(CHO)$ is a metabolic efficiency factor of carbohydrate and wherein $Cc$ is a energy conversion factor of carbohydrate, and
    iv) $W(DF) \times Cdf \times DF(m)$, wherein $W(DF)$ is a metabolic efficiency factor of dietary fiber and wherein $Cdf$ is a energy conversion factor of dietary fiber;
  2) dividing the determined FED value by a factor data obtained from a storage device and saving the result as whole number value for each food product;
f) associating, by the processor of the data processing system, the first and the second food products with a metagroup, wherein the metagroup is determined based at least, in part, on:
  i) a first similarity in nutrients among different food products, and
  ii) a second similarity in usage of different food products within context of a specific diet, and wherein the metagroup is associated with a specific healthfulness formula stored in a storage device of the data processing system, wherein the healthfulness formula is a linear combination of at least a plurality of the following data about nutrients of a food product: i) fat content, ii) sugar content, iii) sodium content, iv) energy, v) saturated fat, and vi) dietary fiber content;
(g) calculating a first healthfulness data for the first food product based on the healthfulness formula of the metagroup via the processor of the data processing system;
(h) calculating a second healthfulness data for the second food product based on the healthfulness formula of the metagroup via the processor of the data processing system;
(i) comparing the first food product to the second food product based at least, in part, on:
  1) the healthfulness data of each food product, and
  2) the whole number value for each food product;
j) determining a daily whole number benchmark data for the human being, wherein the daily whole number benchmark data for the human being is determined based on daily total energy expenditure of the human being;
k) providing an outcome of the comparing step;
l) automatically displaying, by the data processing system, a sum of whole number values of consumed food products, during a day, via a presentation device;
m) during the day, consuming food products until the sum of whole number values of consumed food products is less than or equal to the daily whole number benchmark data saved in said storage device; and
n) repeating at least steps (a)-(m) in successive days to control body weight.

\* \* \* \* \*